US012572802B2

(12) United States Patent
Leube et al.

(10) Patent No.: US 12,572,802 B2
(45) Date of Patent: Mar. 10, 2026

(54) METHODS AND DEVICES IN PERFORMING A VISION TESTING PROCEDURE ON A PERSON

(71) Applicant: Carl Zeiss Vision International GmbH, Aalen (DE)

(72) Inventors: Alexander Leube, Aalen (DE); Dennis Thom, Stuttgart (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/660,605

(22) Filed: May 10, 2024

(65) Prior Publication Data

US 2024/0289616 A1    Aug. 29, 2024

Related U.S. Application Data

(63) Continuation of application No. PCT/EP2023/072660, filed on Aug. 17, 2023.

(30) Foreign Application Priority Data

Aug. 18, 2022    (EP) ..................................... 22191012

(51) Int. Cl.
*G06N 3/08* (2023.01)
*A61B 3/028* (2006.01)
*G06N 20/00* (2019.01)

(52) U.S. Cl.
CPC ............... *G06N 3/08* (2013.01); *A61B 3/028* (2013.01); *G06N 20/00* (2019.01)

(58) Field of Classification Search
CPC ...... G06N 3/08; G06N 3/0455; G06N 3/0464; G06N 20/00; A61B 3/028; G02C 7/027; G16H 50/20
See application file for complete search history.

(56) References Cited

U.S. PATENT DOCUMENTS

| | | |
|---|---|---|
| 10,209,773 B2 | 2/2019 | Khaderi et al. |
| 2019/0197357 A1 | 6/2019 | Anderson et al. |

(Continued)

FOREIGN PATENT DOCUMENTS

| | | |
|---|---|---|
| CN | 106175657 A | 12/2016 |
| CN | 109157186 A | 1/2019 |

(Continued)

OTHER PUBLICATIONS

Li et al., "Spontaneous facial micro-expression detection based on deep learning," IEEE Access, pp. 1130 to 1134, 2016.

(Continued)

*Primary Examiner* — Dave Misir
(74) *Attorney, Agent, or Firm* — Qubit IP, PLLC

(57) ABSTRACT

A computer-implemented method for training of a machine learning model for determining a confidence value during at least one test cycle of a vision testing procedure is disclosed. The confidence value is designated to determine at least one action in at least one subsequent test cycle of the vision testing procedure. Further, a trained machine learning model, a computer program having instructions for training of the machine learning model and a training apparatus are disclosed. Additionally, a computer-implemented method for performing the vision testing procedure on a person, a computer program having instructions for performing the vision testing procedure, a vision test apparatus, and a method for producing a geometrical model of at least one spectacle lens for manufacturing of at least one spectacle lens are disclosed.

18 Claims, 4 Drawing Sheets

(56) References Cited

U.S. PATENT DOCUMENTS

| | | | | |
|---|---|---|---|---|
| 2020/0113736 | A1* | 4/2020 | Bos | G06T 17/00 |
| 2021/0157168 | A1* | 5/2021 | Leube | A61B 3/0025 |
| 2021/0186323 | A1* | 6/2021 | Sarangapani | A61B 3/1015 |
| 2021/0382329 | A1 | 12/2021 | Ohlendorf et al. | |
| 2022/0067353 | A1 | 3/2022 | Matteucci et al. | |
| 2022/0125299 | A1* | 4/2022 | Abou Shousha | G16H 50/70 |
| 2022/0183546 | A1* | 6/2022 | Padula | A61B 3/0041 |
| 2022/0230300 | A1* | 7/2022 | Kawczynski | G06T 7/0004 |
| 2022/0304572 | A1* | 9/2022 | Coveney | G06T 7/0012 |
| 2022/0338728 | A1* | 10/2022 | Skalicky | A61B 3/022 |
| 2022/0354440 | A1* | 11/2022 | Grajales | G16H 50/30 |
| 2023/0296918 | A1* | 9/2023 | Muschielok | G02C 7/028 |
| | | | | 351/159.74 |

FOREIGN PATENT DOCUMENTS

| | | |
|---|---|---|
| CN | 111626319 A | 9/2020 |
| WO | 2017106770 A1 | 6/2017 |
| WO | 2020030722 A1 | 2/2020 |

OTHER PUBLICATIONS

Nagrani et al., "Seeing Voices and Hearing Faces: Cross-modal biometric matching," Proceedings of the IEEE conference on computer vision and pattern recognition, pp. 8427 to 8436, Jun. 2018.
Industrial Norm "Ophthalmic optics–Spectacle lenses—Vocabulary (ISO 13666:2019)," English version EN ISO 13666:2019, Dec. 2019.
Raj et al., "Voice Pathology Detection Based on Deep Neural Network Approach," IOP Conference Series: Materials Science and Engineering, vol. 1020, No. 1, pp. 012001-1 to 012001-6, Jan. 2021.
Syed et al., "Comparative Analysis of CNN and RNN for Voice Pathology Detection," BioMed Research International, vol. 2021, pp. 1 to 8, Apr. 2021.
Jacob et al., "Facial Action Unit Detection With Transformers," Proceedings of the IEEE/CVF Conference on Computer Vision and Pattern Recognition (CVPR), pp. 7680 to 7689, Jun. 2021.
Momin et al., "Recognizing Facial Expressions in the Wild using Multi-Architectural Representations based Ensemble Learning with Distillation," IEEE Access, pp. 1 to 6, Jun. 2017.
Homepage of Keras Applications, available at the url: https://keras.io/api/applications/ (last accessed May 10, 2024).
European Search Report issued in EP 22 191 012.8, to which this application claims priority, mailed May 10, 2023.
Office Action by the European Patent Office (EPO) issued in EP 22 191 012.8, to which this application claims priority, mailed on Oct. 23, 2023.
International Search Report and Written Opinion issued in PCT/EP2023/072660, to which this application claims priority, mailed Jul. 14, 2021.
Intention to grant European patent application EP 22 191 012.8, to which this application claims priority, dated May 7, 2024.
Office Action by the Chinese Patent Office (CNIPA) issued in CN202380015058.0, which is a counterpart hereof, mailed on Jan. 21, 2025, and English-language translation thereof.
Office Action by the Chinese Patent Office (CNIPA) issued in CN202380015058.0, which is a counterpart hereof, mailed on Jul. 12, 2025, and English-language translation thereof.

* cited by examiner

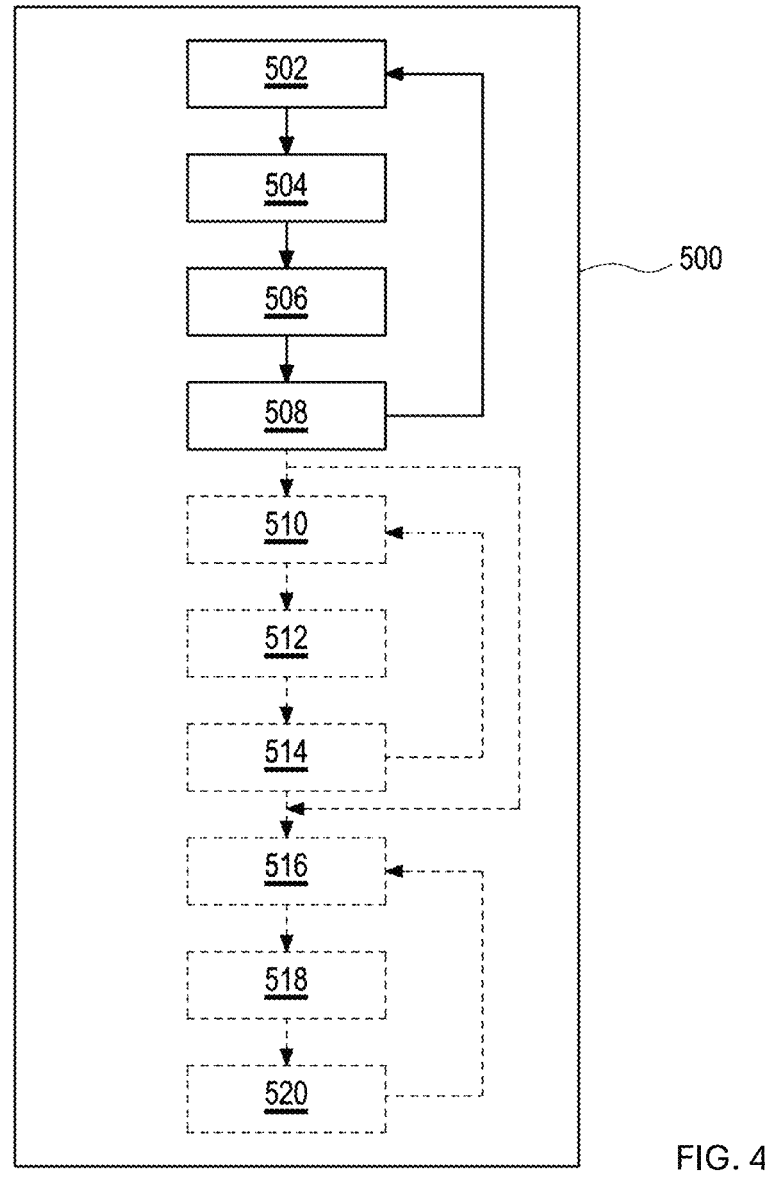
FIG. 4
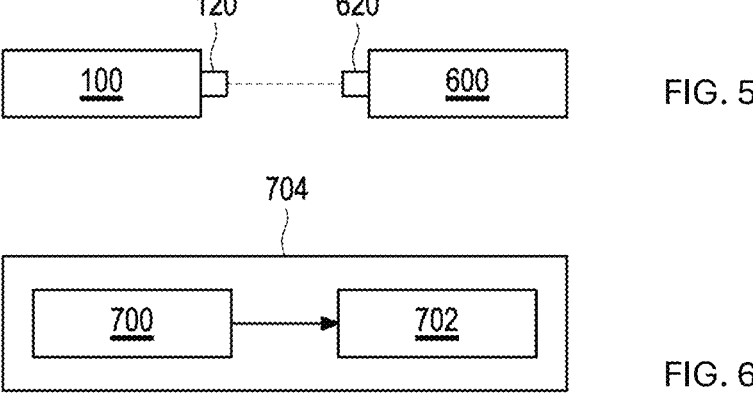
FIG. 5
FIG. 6

METHODS AND DEVICES IN PERFORMING A VISION TESTING PROCEDURE ON A PERSON

CROSS REFERENCE TO RELATED APPLICATIONS

This application is a continuation application of international patent application PCT/EP2023/072660, filed on Aug. 17, 2023 and designating the U.S., which claims priority to European patent application 22 191 012.8, filed on Aug. 18, 2022, both of which are hereby incorporated by reference in their entireties.

TECHNICAL FIELD

The present disclosure relates to a computer-implemented method and a training apparatus for training of a machine learning model for determining a confidence value during at least one test cycle of a vision testing procedure, a computer-implemented method and a vision test apparatus for performing a vision testing procedure on a person, a computer program for training of a machine learning model for determining a confidence value during at least one test cycle of a vision testing procedure, a computer program for performing a vision testing procedure on a person, a trained machine learning model, and a method for producing at least one spectacle lens.

BACKGROUND

U.S. Pat. No. 10,209,773 B2 discloses methods and systems for modifying media, such as Virtual Reality, Augmented Reality, or Mixed Reality (VR/AR/MxR) media based on a vision profile and a target application. In exemplary embodiments of the specification, a Sensory Data Exchange (SDE) is created that enables identification of various vision profiles for users and user groups. The SDE may be utilized to modify one or more media in accordance with each type of user and/or user group.

WO 2017/106770 A discloses methods and apparatuses providing digital diagnostics and digital therapeutics to patients. The digital personalized medicine system uses digital data to assess or diagnose symptoms of a patient, and feedback from the patient response to treatment is considered to update the personalized therapeutic interventions. The methods and apparatus disclosed herein can also diagnose and treat cognitive function of a subject, with fewer questions, decreased amounts of time, and determine a plurality of behavioral, neurological or mental health disorders, and provide clinically acceptable sensitivity and specificity in the diagnosis and treatment.

CN109157186A discloses an unmanned self-help visual acuity monitor including a control host and a display screen communicatively connected to the control host, a wireless interactive keyboard and a binocular camera. The binocular camera includes two sub-cameras that are used for simultaneously collecting face images of the tested persons and transmitting the face images to a control host computer. A non-standard test behavior recognition module is used to identify whether there is non-standard test behavior in the eyes of the tested person according to the face image captured by the binocular camera.

Geethu Miriam Jacob and Björn Stenger, "Facial Action Unit Detection With Transformers," CVPR (2021), pp. 7680 to 7689, describes that the Facial Action Coding System is a taxonomy for fine-grained facial expression analysis. The document proposes a method for detecting Facial Action Units (FAU), which define particular face muscle activity, from an input image. FAU detection is formulated as a multi-task learning problem, where image features and attention maps are input to a branch for each action unit to extract discriminative feature embeddings, using a new loss function, the center contrastive (CC) loss. They employ a new FAU correlation network, based on a transformer encoder architecture, to capture the relationships between different action units for the wide range of expressions in the training data.

Xiaohong Li, Jun Yu, and Shu Zhan, "Spontaneous facial micro-expression detection based on deep learning," 13th International Conference on Signal Processing (2016), IEEE, pp. 1130 to 1134 describes that facial micro-expression refers to split-second muscle changes in the face, indicating that a person is either consciously or unconsciously suppressing their true emotions. Although these expressions are constantly occurring on people faces, they were easily ignored by people with the eye blinking. That is to say, most people do not notice them and it is the true representation of people emotions and mental health. Accordingly, both of psychologists and computer scientists (in the fields of computer vision and machine learning in particular) pay attention to it owing to their promising applications in various fields (e.g., Mental clinical diagnosis and therapy, affective computing). However, detecting micro-expressions is still difficult task. They proposed a novel approach based on deep multi-task learning method with the HOOF (Histograms of Oriented Optical Flow) feature for micro-expression detection. They investigated a deep multi-task learning method for facial landmark localization and split the facial area into regions of interest (ROIS). Facial micro-expression are generated by the movement of facial muscles, so they combined robust optical flow approach with the HOOF feature for evaluating the direction of movement of facial muscles.

Rauf Momin, Ali Shan Momin, Khalid Rasheed, and Muhammad Saqib, "Recognizing Facial Expressions in the Wild using Multi-Architectural Representations based Ensemble Learning with Distillation," IEEE Access (2017), Volume XX describes that facial expressions are the most common universal forms of body language. In the past few years, automatic facial expression recognition (FER) has been an active field of research. However, it is still a challenging task due to different uncertainties and complications. Nevertheless, efficiency and performance are yet essential aspects for building robust systems. They proposed two models, EmoXNet which is an ensemble learning technique for learning convoluted facial representations, and EmoXNetLite which is a distillation technique that is useful for transferring the knowledge from our ensemble model to an efficient deep neural network using label-smoothen soft labels for able to effectively detect expressions in real-time.

Arsha Nagrani, Samuel Albanie, and Andrew Zisserman, "Seeing Voices and Hearing Faces: Cross-modal biometric matching," Proceedings of the IEEE conference on computer vision and pattern recognition (2018), pp. 8427 to 8436 describes that they introduce a seemingly impossible task: given only an audio clip of someone speaking, decide which of two face images is the speaker. In this document they study this, and a number of related cross-modal tasks, aimed at answering the question: how much can they infer from the voice about the face and vice versa? They study this task "in the wild," employing the datasets that are now publicly available for face recognition from static images (VGGFace) and speaker identification from audio (Vox- Celeb). These provide training and testing scenarios for both static and dynamic testing of cross-modal matching. They make the following contributions: (i) they introduce CNN architectures for both binary and multi-way cross-modal face and audio matching; (ii) they compare dynamic testing (where video information is available, but the audio is not from the same video) with static testing (where only a single still image is available); and (iii) they use human testing as a baseline to calibrate the difficulty of the task.

Jeberson Retna Raj, J. Jabez, S. Senduru Srinivasulu, S Gowri, and J S Vimali, "Voice Pathology Detection Based on Deep Neural Network Approach," IOP Conference Series: Materials Science and Engineering (2021), Vol. 1020, No. 1, p. 012001, IOP Publishing, describe that the advancement of technology offers solution to the complex problems faced by the society and brings the wellbeing of the individuals. Smart healthcare is prominent nowadays for diagnosis, treatment and constant monitoring which reduces visitation of hospital, transport cost and waiting time. Voice pathology is a decease which affects the person vocal cord so that one who facing difficult in speech. If the decease not identified in time, it leads to permanent loss of voice for an individual. Traditionally, the decease is identified through oral examination or manual procedures. Due to the advent of smart phone, one can record the voice and send it to the cloud server for processing. Our system classifies the voice data and provides the decision to the user. This greatly reduces the transport cost, and waiting time for oral examination at medical center. The mobile phone recorded the patient voice data and it will be stored into the cloud. The voice data is synthesized to signals and with the help of deep Neural network the voice pathology can be identified.

Sidra Abid Rashid, Munaf Hussain, Samreen Hussain, and Hira Zahid, "Comparative Analysis of CNN and RNN for Voice Pathology Detection," BioMed Research International (2021), Article ID 6635964 describes that diagnosis on the basis of a computerized acoustic examination may play an incredibly important role in early diagnosis and in monitoring and even improving effective pathological speech diagnostics. Various acoustic metrics test the health of the voice. The precision of these parameters also has to do with algorithms for the detection of speech noise. The idea is to detect the disease pathology from the voice. First, they apply the feature extraction on the SVD dataset. After the feature extraction, the system input goes into the 27 neuronal layer neural networks that are convolutional and recurrent neural network (RNN).

In typical vision tests that are performed by a person without the guidance of an experienced professional, the person is left alone with a complicated workflow which has to be performed. In that sense, the person has to respond to several different tasks, e.g., giving an indication of a particular parameter as shape, contrast, size, or orientation for plurality of different symbols. The person may, further, have to adapt different distances between at least one eye of the person and the symbols, which are presented at a presenting device. In such typical vision tests, the behavior of the person during the typical vision tests is not considered. This means that the test strategy is not adapted to the individual needs of the person, as no subsequent action is based on the behavior of the person. Particularly, no individual feedback is provided to the person during the typical vision test based on the behavior of the person. The person, therefore, tends not to trust in the result of such typical vision tests.

SUMMARY

It is an objective of the present disclosure to provide a computer-implemented method and a training apparatus for training of a machine learning model for determining a confidence value during at least one test cycle of a vision testing procedure, a computer-implemented method and a vision test apparatus for performing a vision testing procedure on a person, a computer program for training of a machine learning model for determining a confidence value during at least one test cycle of a vision testing procedure, a computer program for performing a vision testing procedure on a person, a trained machine learning model, and a method for producing at least one spectacle lens, which at least partially overcome the above-mentioned problems of the related art.

It is a particular objective of the present disclosure to provide an easily accessible and trustworthy vision testing procedure that offers a precise, fast, and reliable approach, which is obtained by a training procedure, which better addresses the actual problems typically occurring in vision testing. It is especially desired that, after training, the corresponding vision testing procedure can, eventually, be performed in a guided manner which provides an easily accessible and comprehensible approach to the person who is queried, which, thereby, considerably contributes to reliable and reproducible results obtained in vision testing, and which, eventually, leads to producing of better adapted spectacle lenses to the needs of the person who is queried.

This problem is solved by a computer-implemented method and a training apparatus for training of a machine learning model for determining a confidence value during at least one test cycle of a vision testing procedure, a computer-implemented method and a vision test apparatus for performing a vision testing procedure on a person, a computer program, a trained machine learning model, and a method for producing at least one spectacle lens wherein at least one parameter of the machine learning model that resulted by determining a minimal deviation is used in the trained machine learning model. Exemplary embodiments, which might be implemented in an isolated fashion or in any arbitrary combination, are set forth throughout the following description.

In a first aspect, the present disclosure relates to a computer-implemented method particularly suitable for training of a machine learning model for determining a confidence value during at least one test cycle of a vision testing procedure, wherein the confidence value is designated for determining at least one action in at least one subsequent test cycle of the vision testing procedure; comprising the following steps:

a) providing training data, comprising
  first information about at least one behavior of a person during at least one test cycle of a vision testing procedure, wherein the at least one behavior of the person as provided by the first information is recorded from an observation of the person during a time interval after the person is queried to solve at least one task by providing an expected response;
  second information about at least one known confidence value;

b) determining at least one confidence value of the person, wherein the confidence value is a measure of a confidence level of the person at providing the expected response, by analyzing the first information using a machine learning model, and determining a deviation between the determined confidence value and the at least one known confidence value as provided by the second information;

c) adjusting the machine learning model for minimizing the deviation between the determined confidence value and the at least one known confidence value;

wherein the steps a) to c) are repeated until a determination criterion is met.

Herein, the indicated steps may, typically, be performed in the given order, commencing with step a) and finishing with step c). However, any or all of the indicated steps may also be repeated several times and/or preformed concurrently in part.

As generally used, the term "computer-implemented method" refers to a method which involves at least one apparatus, specifically a computer, or a plurality of apparatus, particularly connected via a computer network. The plurality of apparatus may be connected via a network by using at least one connection interfaces at any one of the apparatus of the plurality of apparatus. The computer-implemented method may be implemented as at least one computer program that may be provided on a storage medium carrying the computer program, whereby at least one of the steps of the computer-implemented method, specifically at least one of steps a), b), or c), are performed by using the at least one computer program. Typically any one of the steps a), b), and c) are performed using the at least one computer program. Alternatively, the at least one computer program may be accessible by an apparatus which may be adapted for performing the method via a network, such as via an in-house network or via internet. With particular regard to the present disclosure, the present method can, thus, be performed on a programmable apparatus which is configured for this purpose, such as by providing a computer program which is configured for such a purpose.

As generally used, the term "machine learning model" refers to a trainable computer-implemented architecture, particularly a trainable statistical model, that applies artificial intelligence to automatically determine a representative result, particularly the confidence value. As generally used, the term "training" refers to a process of determining adjustable parameters of the machine learning model using a training data for generating a trained machine learning model. The training may comprise at least one optimization or tuning process, wherein a best parameter combination is determined. The training is carried out to improve the capability of the machine learning model to determine the representative result, particularly the confidence value, by analyzing at least a portion of the training data.

As generally used, the term "determine" or any grammatical variation thereof refers to a process of generating representative results. With particular regard to the present disclosure, the representative results generated by the present aspect is information about the confidence value of the person. The information may be provided as data. The term "data" refers to an item, such as a numeric or an alphanumeric item, which comprises at least one piece of information. The data may be provided in machine readable form, such that it may be input or output of a machine learning model, particularly of any neural network comprised by the machine learning model.

As used herein, the term "vision testing procedure" refers to a procedure in which the at least one condition, particularly of at least one eye, of the person is determined, wherein the at least one condition is a performance indicator of the vision of the person, particularly an impairment of the vision of person. The at least one condition of the at least one eye of the person may be at least one visual parameter of the at least one eye of the person. The vision testing procedure may be performed in a stepwise manner, particularly as a series of consecutive test cycles. As used herein, the term "performance indicator of the vision of the person" refers to a value used for defining a visual ability of the person, particularly a visual parameter of the at least one eye of the person. As used herein, the term "subsequent test cycle" refers to a test cycle which is performed after at least one particular test cycle. The at least one "particular test cycle" may be the test cycle that is currently performed. The at least one particular test cycle may, thus, be performed before the subsequent test cycle. In the subsequent test cycle, an action may be performed that is based on the confidence value. As used herein, the term "action" refers to a process step that is, particularly directly, related to the vision testing procedure, specifically a progress of the vision testing procedure and/or a collection of further training data. As used herein, the term "confidence value" refers to a measure of a certainty level of the person at providing the expected response. Thereby, the confidence value indicates how sure the person is in giving an expected response during at least one cycle of the vision testing procedure and/or whether the given response was correct compared to the query.

According to step a), training data is provided. Firstly, the training data comprises first information about at least one behavior of a person during at least one test cycle of a vision testing procedure, wherein the at least one behavior of the person as provided by the first information is recorded from an observation of the person during a time interval after the person is queried to solve at least one task by providing an expected response. Further, second information about at least one known confidence value is comprised by the training data, wherein the confidence value is a measure of a confidence level of the person at providing the expected response.

As generally used, the term "training data" refers to data that is used for training of the machine learning model. The parameters of the machine learning model may, thus, be adjusted, when at least a portion of the training data is analyzed by the machine learning model. The training data, in that sense, may comprise at least one "known" information and the machine learning model may, further, be configured for a training of determining information that corresponds to the known information as accurate as possible, or, in other words, the determined information may deviate from the known information as little as possible. The training data may comprise real data and/or simulated data.

As used herein, the term "information" refers to a piece of content being comprised by data. As used herein, the terms "first" or "second" or "third" and so forth are considered as a description of an element without specifying an order or a chronological sequence and without excluding a possibility that other elements of the same may be present. The presence of an element with a higher number does not imply that an element with a lower number has also to be present, e.g., the presence of a "second" element does not imply presence of a "first" element. Still, a "first" element may be present. A "first" element is generally different from a "second" element and a "third" element. This is true for any possible permutation.

As used herein the term "behavior" refers to an observable action and/or reaction of the person, including not acting and/or not reacting, particularly to the at least one task that the person is being queried to solve. The acting and/or reacting of the person may be understood as a kind of communication of the person, specifically any verbal communication and any non-verbal communication, which may comprise body language.

As used herein, the term "recording" or any grammatical variation thereof refers to a generation of data comprising a specific information, particularly the training data comprising the first information. Particularly for the training data, the term "recording" does not necessarily imply that the first information being recorded from an observation is real data, in particular, the first information being recorded from the observation may be simulated data, particularly simulated by simulating the observation. As used herein, the term "observation" refers to monitoring a person. Herein, the monitoring may be selected from at least one of: recording at least one image, at least one video clip of the person, recording the voice of the person, or recording at least one vital sign of the person. The recording may be performed when the person is trying to give the expected response.

As used herein, the term "querying" or any grammatical variation thereof refers to a process of requesting a response or an indication from a person, particularly for solving at least one task. The requesting may be performed, in particular, by presenting a request. The request may be presented during the particular test cycle. The request may be at least one of: a visible, an audible, or a tactile request. As further used herein, the term "solving" or any grammatical variation thereof refers to a person being required to provide an expected response for solving at least one task. The term "expected response" refers to the fact that for solving the task, providing a specific response is required. The specific response may be a correct response that is solving the at least one task correctly. As an alternative, the specific response may be an incorrect response solving the at least one task incorrectly. Thereby, providing no response by the person who is queried to the at least one task may also be considered as an incorrect response. The response may be considered as incorrect if the behavior of the person is interpreted as uncertain. As a result, a correct response or an incorrect response to the at least one task may be expected to be provided by the expected response.

As used herein, the term "time interval" refers to a duration or a time period having a first point of time, at which the duration starts, and a second point of time, at which the duration finishes. In particular, the time interval may start at the first point of time when the person is queried to provide the expected response. The time interval may end at the second point of time when the person has provided the expected response or when a predetermined time-to-answer has expired.

According to step b), the at least one confidence value of the person is determined by analyzing the first information by using a machine learning model. Further, a deviation between the determined confidence value and the at least one known confidence value as provided by the second information is determined. Thereby, the deviation may be determined by a loss-function and/or an objective-function may be used.

As generally used, the term "analyzing" or any grammatical variation thereof refers to a systematic investigation in which the at least one outcome under investigation is broken down into its components. These components are, hereby, investigated on the basis of selected criteria and subsequently ordered, examined and evaluated. As generally used, the term "deviation" refers to a difference between two pieces of information, typically the difference between two values, particularly a mathematical and/or statistical difference between the two values. The deviation as used in step b) is the difference between the determined confidence value and the at least one known confidence value.

According to step c), the machine learning model is adjusted for minimizing the deviation between the determined confidence value and the at least one known confidence value. Further, steps a) to c) are repeated until a determination criterion is met.

As used herein, the term "adjusting" or any grammatical variation thereof refers to changing at least one parameter of the machine learning model. The at least one parameter may be changed in order to minimize the deviation between the determined confidence value and the at least one known confidence value, particularly on a statistical basis. As used herein, the term "determination criterion" refers to a condition that, when met, leads to the termination of a sequential or iterative procedure, particularly the termination of the computer-implemented method for training of a machine learning model. The at least one parameter of the machine learning model that resulted by determining a minimal deviation may be used in a trained machine learning model.

In an exemplary embodiment, the determination criterion may be selected from:

the deviation being below a threshold;

a difference between the deviation determined in a training cycle and the deviation determined in a preceding training cycle being below a further threshold, wherein a training cycle comprises the steps a) to c);

a predetermined number of the training cycles is reached; or an end of a predetermined training time interval is reached.

As used herein, the term "threshold" refers to a maximal deviation that is allowable before the computer-implemented method for training of a machine learning model is terminated. As used herein, the term "difference" refers to a variance between deviations determined in two different training cycles. As used herein, the term "training cycle," which may also be referred to as training epoch, refers to a sequence of the steps a) to c). As used herein, the term "further" refers to an additional instance of an item. As generally used, the term "predetermined" refers the quantity being established and/or decided in advance, particularly the number of training cycles and/or the training time interval being decided before the computer-implemented method for training of a machine learning model is started.

In a further exemplary embodiment, an indication about the second information may be obtained from at least one of:

a professional who is experienced in performing the vision testing procedure;

the person, particularly after being queried during the vision testing procedure to provide an indication about the confidence value;

monitoring at least one vital sign of the person, particularly wherein the at least one vital sign is selected from any one of a blood pressure; a heart-beat rate or a blink rate; or a time value required for the person to provide the response, particularly the expected response.

As generally used, the term "professional" refers to an expert having an above-average knowledge in a subject area or in several specific subject areas, or who possesses special skills. As generally used, the term "experiencing" or any grammatical variation thereof refers to the professional who is practiced in performing the vision testing procedure, particularly frequently performing the vision testing procedure on a regular basis. As used herein, the term "indication" refers to a detail or an information directly and/or indirectly related to the feature the indication is about. The indication may thus be the feature itself or a paraphrase of the feature.

In particular, the person who is queried may, especially, be asked not only to provide the result of the at least one task but also to indicate how confident he or she is about the correctness of the result. As generally used, the term "monitoring" refers to a process of observing or checking an observable, particularly on a regular basis and/or continuous basis. As generally used, the term "vital sign" refers to perceptible and testable or measurable life functions of the person, which provide information about vital body functions. As used herein, the term "time value required for the person to provide the response" may refer to a time interval, particularly a time interval that starts when the expected response is queried from the person and/or ends when the response is provided, particularly the expected response.

In a further exemplary embodiment, the professional may be at least one of:
an optician;
an ophthalmologist;
a technician;
a psychologist; or
a nurse.

As generally used, the term "optician" refers to a technical practitioner who designs, fits and dispenses spectacle lenses for a correction of the vision of the person. As generally used, the term "ophthalmologist" refers to a physician who specializes in eye care. As generally used, the term "technician" refers to a person working in a field of technology who is experienced in the relevant skill and/or technique, particularly in the skill and/or technique of spectacle lenses and/or performing vision testing procedures. As generally used, the term "psychologist" refers to a professional who practices psychology. As generally used, the term "nurse" refers to a professional working in the health care sector. In particular, a team comprising at least two professionals from the mentioned list can also be used for the purposes of the present disclosure.

In a further exemplary embodiment, the machine learning model may, further, be trained for determining a correctness value, wherein the at least one correctness value is a measure of a probability that a response provided by the person is the expected response,
wherein the first information further comprises information about the response provided by the person, and
wherein the training data further comprises third information about at least one known correctness value;
wherein the at least one correctness value is determined by analyzing the first information using the machine learning model, wherein a first further deviation is determined between the determined correctness value and the known correctness value as provided by the third information, and wherein the further training is repeated until a first further determination criterion is met. As used herein, the term "correctness value" refers to a measure of a probability that a response provided by the person is the expected response. The correctness value may be correlated with the confidence value, particularly in such a manner that a person being unsure on giving the expected response, specifically the correct response, is more likely to give an incorrect response, and vice versa.

In a further exemplary embodiment, the first further determination criterion may be selected from:
the first further deviation being below a first further threshold;
a difference between the first further deviation determined in a training cycle and the first further deviation determined in a preceding training cycle being below a first further threshold, wherein a training cycle comprises the steps a) to c);
a predetermined first further number of the training cycles is reached; or
an end of a predetermined first further training time interval is reached.

In a further exemplary embodiment, the machine learning model may comprise
a first neural network configured for determining the confidence value; and/or
a second neural network configured for determining the correctness value,
particularly wherein the first neural network differs from the second neural network.

As generally used, the term "neural network" refers to an artificial network, particularly comprising a plurality of nodes, which are, typically, interconnected by at least one edge for transferring data between at least two of the nodes. A neural network, specifically the first and/or the second neural network, may be comprised by or be the machine learning model. The manner according to which data is transferred between the nodes and/or processed within the nodes may be influenced by the at least one parameter of the machine learning model, specifically the at least one parameter of the first neural network and/or of the second neural network. A neural network may comprise an input layer for inputting the data to be analyzed. A neural network may, additionally, comprise an output layer for outputting a determined data. As used herein, the term "plurality" refers to a quantity of at least two units, typically more than two units, particularly a quantity of least two pieces, typically of more than two pieces, of the second information.

In a further exemplary embodiment, the machine learning model may, further, be trained for determining at least one action in at least one subsequent test cycle of the vision testing procedure, wherein the training data further comprises
fourth information about at least one known action,
wherein the at least one action is determined by analyzing the at least one determined confidence value by using the machine learning model, wherein a further deviation is determined between the at least one determined action and the at least one known action provided by the fourth information, wherein the further training is repeated until a second further determination criterion is met.

In a further exemplary embodiment, the second further determination criterion may be selected from:
the second further deviation being below a second further threshold;
a difference between the second further deviation determined in a training cycle and the second further deviation determined in a preceding training cycle being below a second further threshold, wherein a training cycle comprises the steps a) to c);
a predetermined second further number of the training cycles is reached; or
an end of a predetermined second further training time interval is reached.

In a further exemplary embodiment, the machine learning model may further comprise
a third neural network for determining the at least one action,
particularly wherein the third neural network differs from the first neural network and from the second neural network.

In a further exemplary embodiment, determining the at least one action may comprise additionally analyzing the at least one correctness value. In a further exemplary embodiment, the fourth information about the at least one known action may be determined in an assessment of the professional experienced in performing the vision testing procedure. As used herein, the term "assessment" may refer to a process of collecting the information based on an estimation of the professional.

In a further exemplary embodiment, the machine learning model may be a machine learning model that is trained in a domain applicable to the vision testing procedure before it is trained for determining the at least one confidence value according to any one of the preceding aspect or exemplary embodiments. As used herein, the term "trained in a domain applicable to the vision testing procedure" refers to the fact that the machine learning may be trained for analyzing comparable, specifically the same, input data and/or for determining comparable output data. Thereby, the effort for training the machine learning model for determining the at least one confidence value may be reduced.

In a further exemplary embodiment, the domain applicable to the vision testing procedure may be selected from at least one of:

voice classification or voice regression;

facial expression classification or facial expression regression; or body expression classification or body expression regression.

As generally used, the term "classification" refers to a determination of a respective value on a discrete scale. As used herein, the term "regression" refers to a determination of a respective value on a continuous scale.

In a further aspect, the present disclosure relates to a computer-implemented method, particularly suitable, for performing a vision testing procedure on a person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding aspect or exemplary embodiments by using a processing device; and g) determining at least one action in at least one subsequent test cycle of the vision testing procedure based on the determined confidence value by using the processing device.

As used herein, the term "test cycle" refers to a sequence of the steps d) and e), particularly including step f) and/or step g). As used herein, the term "presenting" refers to displaying the at least one task to the person. As used herein, the term "presentation device" refers to a device configured for displaying the at least one task to the person. As used herein, the term "recording device" refers to a device configured for generating the measurement data. As used herein, the term "processing device" refers to an electronic device configured for processing data for determining a result, particularly configured for processing the measurement data, specifically for determining the at least one action. A processing device may be a processing unit, specifically a central processing unit, of a programmable apparatus, specifically a computer. The processing unit may be a processor and/or an electronic circuit, which particularly may execute executable instructions comprised by a computer program. The term "based on the determined confidence value" refers to the at least one further action being determined by considering the determined confidence value. Thereby the at least one further action is depending on the confidence value.

In a further exemplary embodiment, steps d) to f) may be repeated in at least one subsequent test cycle using the at least one determined action.

In a further exemplary embodiment, the confidence value may be selected from at least one discrete scale, particularly wherein the confidence value is selected from at least two individual values; or at least one continuous scale, particularly wherein the continuous scale is ranging from the person being fully confident to the person being fully unsure.

As used herein, the term "discrete scale" refers to a range on which a plurality of different features is arranged, whereby a feature may be further subdivided for increasing the information content of the range, whereby further features are generated and the resolution of the discrete scale increases. In case the confidence value may be considered as a feature, a range of conceivable characteristics of the confidence value may be comprised in a feature. The term "continuous scale" refers to a range on which a plurality of different features is arranged, whereby a feature cannot be further subdivided for increasing the information content of the range. In the case the confidence value may be considered as a feature, exactly one conceivable characteristics of the confidence value may be comprised in exactly one feature.

In a further exemplary embodiment, a first value of the confidence value may represent the person being confident, and a second value of the confidence value may represent the person being unsure about providing the expected response. Thereby exactly two different values, namely the first value and the second value, may be available on a discrete scale. As used herein, the term "confident" refers to the person being sure on providing the expected response. As used herein, the term "unsure" refers to the person being insecure, or not confident at all, when providing the expected response. In a further exemplary embodiment, the confidence value may be selected from at least three individual values.

In a further exemplary embodiment, a first value of the confidence value may represent the person being confident, and/or a second value of the confidence value may represent the person being neutral, and/or a third value of the confidence value may represent the person being unsure about providing the expected response. Thereby exactly three different values, namely the first value, the second value and the third value, may be available. As used herein, the term "neutral" refers to the person being balanced in terms of providing the expected response, thereby the person being neither confident nor unsure on providing the expected response. However, further exemplary embodiments are conceivable.

In a further exemplary embodiment, the at least one known confidence value as provided by the second information may have the same number of values as the determined confidence value; and/or wherein the individual values of the at least one known confidence value as provided by the second information may represent the same piece of information about the confidence value as the values of the determined confidence value.

As used herein, the term "same number of values" refers to the respective value having the same amount of features on a respective scale. As used herein, the term "represent the same piece of information about the confidence value" refers to each value of the known confidence value comparing and/or being compatible to a value of the determined confidence value. By way of example, the confidence value may be selected from a percentage of 0% being assigned to "not confident" via 50% being assigned to "neutral" up to 100% being assigned to "confident." However, further exemplary embodiments and examples are conceivable.

In a further exemplary embodiment, the time interval starts at a first point of time when the person may be queried to provide the expected response. As used here, the term "queried to provide the expected response" may refer to a point in time at which the response from the person is requested. The point of time at which the request is started and/or ended may be the "first point of time." In a further exemplary embodiment, the time interval may end at a second point of time after which the person has provided the response and/or at which a predetermined time-to-answer has expired. As used herein, the term "provided the expected response" may refer to the point of time at which the person has stopped giving the response, particularly the expected response. As used herein, the term "time-to-answer" refers to a time interval in which the person can provide the expected response. Herein, a duration of this time interval may be a predetermined fixed value, or may be adjusted in accordance with a duration a particular person may actually need for the at least one task. By way of example, a value for this time interval may be changed depending on a time value required for the person to provide the response, especially being increased in if the person may show a high rate of providing no response to the at least one task.

In a further exemplary embodiment, the at least one determined action may be used in at least one consecutive test cycle. As generally used, the term "consecutive test cycle" refers to a test cycle that is performed directly after a particular test cycle without any intermediate, the further test cycle being performed after the particular test cycle and before the consecutive test cycle. Thereby, the consecutive test cycle is the next test cycle that is performed after the particular test cycle.

In a further exemplary embodiment, the at least one action may be determined by at least one of
the machine learning model trained by the method according to any one of the preceding aspect or exemplary embodiments by using the processing device;
the professional performing the vision testing procedure; or
a predetermined response-action scheme, particularly by using the processing device.

As used herein, the term "predetermined response-action scheme" refers to at least one instruction, particularly a plurality of instructions, on how to perform the vision testing procedure, particularly at least one instruction comprising information about the at least one action is to be performed in the subsequent test cycle on basis of the determined confidence value, particularly in the particular test cycle.

In a further exemplary embodiment, the measurement data may further comprise fifth information about the response, especially the actual response, as provided by the person to the at least one task. In a further exemplary embodiment, the fifth information may be comprised by the first information. As used herein, the term "fifth information" refers to a piece of information that may be comprised in the first information. The fifth information may, in particular, be recorded during an observation of the person.

In a further exemplary embodiment, the at least one action may be further based on at least one of:
the at least one correctness value;
the time value required for the person to provide the response, particularly the expected response;
the at least one presented task; or
the progress of the visual testing procedure.

In a further exemplary embodiment, at least one of
the at least one confidence value;
the at least one correctness values;
the at least one action; or
the at least one presented task
may be stored in a data storage unit.

In a further exemplary embodiment, wherein the determining at least one action in at least one subsequent test cycle may be based on at least one of:
a predefined number of a plurality of confidence values;
a predefined number of a plurality of correctness values;
a predefined number of a plurality of actions; or
a predefined number of a plurality of presented tasks,
particularly performed in at least 2, 5, 10, 20 or 30 different measurements.

In a further exemplary embodiment, the least one correctness value may be selected from at least two individual values. Thereby, the correctness value may be selected from a discrete scale comprising exactly the two individual values. On the other hand, the correctness value may further be selected from a continuous scale comprising the two individual values. In particular, the definitions and examples that are provided above in relationship with the confidence value may also be applicable here.

In a further exemplary embodiment,
a first value may represent the response as provided by the person is the expected response, and/or
a second value may represent the response as provided by the person is not the expected response.

Thereby exactly two different values, namely the first value and the second value, may be available. Further, providing no response by the person who is queried to the at least one task may also be considered as not being the expected response.

In a further exemplary embodiment, the vision testing procedure may be performed to determine at least one condition, particularly of at least one eye, of the person, particularly wherein the condition may be an performance indicator of the vision of the person, particularly an impairment of the person. As used herein, the term "condition" may refer to a state of mind and/or body of the person. It may, particularly, not refer to a sickness and/or health status of the person requiring any medical procedure. As generally used, the term "impairment" refers to a loss and/or an abnormality of physiological, psychological, or anatomical structure and/or function, whether permanent or temporary. An impairment is, particularly, a condition related to the vision of the person, particularly to the at least one eye of the person, that may be considered as not being normal, and/or may be perceived as disadvantageous by the person and/or may be possibly improved.

In a further exemplary embodiment, the at least one condition of the at least one eye of the person may be at least one visual parameter of the at least one eye of the person. As used herein, the term "visual parameter" refers to a refractive error and/or a visual performance of the at least one eye of the person.

In a further exemplary embodiment, the at least one visual parameter may be selected from at least one of a refractive error and/or a visual performance of the at least one eye of the person. As generally used, the terms "refraction" or "refractive" refer to a bending of incident light entering the interior of the eye of the person via the pupil, wherein the term "refractive error" refers to an observation that the incident light may, in particular owing to a form of the eye, not be focusing appropriately on the retina of the eye, resulting in a defocus of the eye. As used herein, the term "visual performance" refers to a characteristic that is indirectly and/or directly related to the at least one eye of the person, wherein the visual performance may be determined by investigating the at least one eye of the person by using an adapted measurement procedure.

In a further exemplary embodiment, the refractive error of the at least one eye of the person may be at least one of a value related to:

a spherical power;

a cylindrical power;

a cylinder axis; or an addition power.

Based on standard ISO 13666:2019 (referred to "Standard" in the following), Section 3.12.2, the term "spherical power," usually abbreviated to "sphere" or "sph," refers to a value of a back vertex power of a spherical-power lens, or for a back vertex power in one of two principal meridians of an astigmatic-power lens, depending on a principal meridian chosen for reference. The spherical power of the at least one eye of the person may be a value related to a "spherical equivalent." As based on the Standard, Section 3.13.7, the term "cylindrical power," usually abbreviated to "cylinder" or "cyl," refers to an algebraic difference between principal powers with power of the principal meridian chosen for reference being subtracted from the other principal power. As based on in the Standard, Section 3.13.8, the term "cylinder axis," usually abbreviated to "cyl axis" or "axis," refers to a direction of the principal meridian of a lens whose vertex power is chosen for reference. As based on in the Standard, Section 3.16.3, the term "addition power," "addition" also abbreviated to "add," refers to a difference between the vertex power of a near portion and the vertex power of a distance portion in a multifocal or power-variation lens.

In a further exemplary embodiment, the visual performance may be selected from at least one of a visual acuity, particularly selected from at least one of:

a near field visual acuity;

an intermediate field visual acuity; or a far field visual acuity;

a contrast sensitivity; or a color vision; or a visual field.

As generally used, the term "visual acuity" refers to a spatial resolution ability of the at least one eye of the person with respect to a structure within at least one visual target. As generally used, the "near field" refers to a distance of up to 40 centimeters, and typically up to 25 centimeters. As generally used, the "intermediate field" refers to a distance of up to 2 meters or 4 meters, and typically of at least 40 centimeters. As generally used, the "far field" refers to a distance of at least 4 meters. As further generally used, the term "contrast sensitivity" refers to a ability of at least one eye of a person to discern between different luminance levels in at least one visual target. As further generally used, the term "color vision" refers to a ability of the at least one eye of the person to discern between different colors or wavelengths of light comprised by at least one visual target. As generally used, the term "visual field" refers to a spatial area which is perceptible by the at least one eye of the person. The visual field comprises the central field of view and the peripheral field of view.

In a further exemplary embodiment, the at least one expected response may be at least one of:

a verbal indication of a solution of the at least one task;

a non-verbal indication of a solution of the at least one task.

As used herein, the term "verbal indication" refers to an audible response provided by the person who is queried in form of a sound, particularly provided by the person speaking. As further used herein, the term "non-verbal indication" refers to a further type of response which is provided by using a different manner of communication apart from the person speaking. As particularly used herein, the term "non-verbal indication" may, thus, comprise a further part of the communication that is, unintentionally or intentionally, be conveyed by the person speaking.

In a further exemplary embodiment, the first information may comprise only information recorded in a time interval during which the at least one person is providing the response. In a further exemplary embodiment, the first information may be processed in a pre-processing routine to comprise only information about a predetermined body-part of the person, particularly selected from at least one of: the face of the person; or the upper body of the person. In a further exemplary embodiment, the first information may be processed in a pre-processing routine to comprise only information about the person showing a predetermined at least one behavior.

In a further exemplary embodiment, the first information about the at least one behavior, particularly the at least one predetermined behavior, of the person may comprise information about at least one of:

at least one expression in a body of the person, particularly at least one expression in a face of the person;

at least one expression in the voice of the person;

a characteristic behavior of a head of the person, particularly causing a movement of the at least one eye towards or away from the presentation device;

a characteristic behavior of a movement of the at least one eye of the person;

a characteristic behavior of an eyelid of the at least one eye of the person;

a characteristic behavior of at least one arm of the person.

As generally used, the term "expression in a body" refers to a form of non-verbal communication, particularly at least one of: a gesture, an expression in the face, a posture, a habitus and/or further conscious or unconscious expressions. As generally used, the term "expression in a face" refers to at least one visible movement of the facial surface and or feature, particularly including no visible movement of the facial surface at all. As generally used, the term "expression in the voice" refers to a characteristic of the voice, particularly the speech of the person. As used herein, the term "characteristic" may refer to a specific pattern, particularly a pattern that is being performed in a repetitive manner. As used herein, the term "movement of the at least one eye of the person" may refer to a change in the line of sight of the person. Based on the "Standard," Section 3.2.24, the term "line of sight" refers to a path from a point of interest, i.e. a point of fixation, in object space to a center of an entrance pupil of the eye of the person and, further, comprise a continuation in image space from a center of an exit pupil to a retinal point of fixation, generally the foveola, in the eye of the person. As generally used, the term "eyelid" refers to a thin fold of skin that covers and protects the at least one eye of the person.

In a further exemplary embodiment, the at least one expression in the body of the person may be selected from at least one of:

at least one expression in the face of the person; particularly an expression of the at least one eye of the person, particularly an eye squinting of the person;

a scratching of the head, particularly by using a hand of the person; or the head of the person moving closer to or away from the presentation device, particularly for thereby adjusting a distance between the at least one eye of the person and the presentation device.

As used herein, the term "eye squinting" refers to the action of looking at something with partially closed eyes.

In a further exemplary embodiment, the at least one expression in the voice may be selected from at least one of:

a volume;

a time duration;

an irregular pause;

a frequency or pitch, particularly a mean frequency or pitch;

a modulation.

As generally used, the term "volume" refers to an intensity or amplitude of the voice.

As used herein, the term "time duration" refers to a time interval of the person giving the response, particularly starting when the person begins to give the response and/or ending when the person terminates giving the response and/or commences giving at least a portion of the response. As used herein, the term "irregular pause" refers to an unexpected break of the person in giving the response, particularly a stutter. As used herein, the term "frequency" refers to a pitch of a tone, particularly the speech and/or voice of the person. As used herein, the term "modulation" refers to an adjusting of the voice for a shaping of the speech.

In a further exemplary embodiment, at least one recording device may be selected from at least one of:

an audio recording device;

a visual recording device;

a tactile recording device; or a distance recording device.

As used herein, the term "audio recording device" refers to a device configured for recording audio data of the person, particularly from an observation of the person. The audio data may include the voice of the person, particularly the provided response of the person may be comprised in the recorded audio data, specifically comprised in the first information. As used herein, the term "visual recording device" refers to a device configured for recording visual data of the person, particularly from an observation of the person, particularly a camera. The visual data may include at least one of: the body, or the face of the person, particularly the provided response of the person may be comprised in the recorded visual data, specifically comprised in the first information. As used herein, the term "tactile recording device" refers to a device configured for recording tactile data of the person, particularly from an observation of the person. The tactile data may include the person touch sensitive device, particularly a touchpad or a button, specifically for giving the response. As used herein, the term "distance recording device" refers to a device configured for recording distance data of the person, particularly from an observation of the person, particularly selected from at least one of: at least one depth sensor; a stereo camera; or a LiDAR sensor. The distance data may include the distance between the at least one eye of the person and the presentation device. As used herein, the term "LiDAR sensor" refers to a measurement device for optical distance and/or velocity measurement.

In a further exemplary embodiment, the at least one expression in the voice of the person may be recorded by using the audio recording device, particularly a microphone. As generally used, the term "microphone" refers to a sound converter that converts sound pressure oscillations from the air into corresponding electrical voltage changes.

In a further exemplary embodiment, the at least one expression in the body of the person may be recorded by using the visual recording device, particularly selected from at least one of:

a camera, particularly at least one of a front camera and/or a back camera of a mobile communication device, specifically selected from at least one of:

a smartphone;

a tablet; or a smart watch;

a photo-camera;

an infrared-camera;

a webcam;

eye tracking glasses; or a visually evoked potential device.

As generally used, the term "camera" refers to an optical device that captures visual images.

As generally used, the term "mobile communication device" refers to a portable wireless telecommunications equipment that may transmit and/or receive voice, video, or computer data, specifically being a smartphone. As generally used, the term "smartphone" refers to a mobile phone having extensive computer functionalities and connectivity. As generally used, the term "photo-camera" refers to a device for taking and/or storing at least one image and/or a short series of images. As generally used, the term "infrared-camera" refers to a camera that is configured for recording at least one image of at least a portion of the infrared spectrum and/or the infrared spectrum. As generally used, the term "webcam" refers to a small camera that may be placed on or in a monitor, or may be introduced into a computer. As generally used, the term "eye tracking glasses" refers to a spectacle having an attached sensor for tracking an eye, particularly an eye movement. As generally used, the term "visually evoked potential device" refers to a device configured for recording of a specific part of the nervous system.

In a further exemplary embodiment, solving the at least one task may be performed by the person using at least one assistive device, particularly at least one assistive device having a degree of influencing the ability of the person to solve the at least one task. As generally used, the term "assistive device" refers to a device configured for supporting the person in solving the at least one task. In a further exemplary embodiment, the at least one assistive device may be configured to counteract the impairment of the person impeding the person to solve the at least one task. As used herein, the term "counteract" refers to a use of the assistive device which results in decreasing the impairment of the person.

In a further exemplary embodiment, at least one assistive device may be selected from at least one of:

a visual aid, particularly an optical lens, used by the person; or a phoropter;

a spectral filter;

a polarization filter; or a liquid optical lens device.

As generally used, the term "visual aid" refers to a device that is configured for improving the capability of the person to see, particularly thereby improving the vision of the person. A typical visual aid may be an optical lens. As generally used, the term "phoropter" refers an ophthalmic testing device. A phoropter may also be known as refractor. As generally used, a "filter" is commonly used to select or eliminate specific information, particularly spectral information about a wavelength of light and/or polarization information about a polarization of the light. As generally used, the term "liquid optical lens device" refers to a device comprising at least one cell or a plurality of cells that are mechanically or electrically controlled and contain optical-grade liquid.

In a further exemplary embodiment, the degree of the at least one assistive device of influencing the ability of the person to solve the at least one task may be selected from:

at least one refractive value of the visual aid used by the person when solving the at least one task;

at least one refractive value of the phoropter or the liquid optical lens used by the person when solving the at least one task;

at least one spectral characteristic of a spectral filter used by the person when solving the at least one task; or at least one polarization characteristic of a polarization filter used by the person when solving the at least one task.

As used herein, the term "refractive value" refers to a characteristic chosen to counteract a refractive error as defined above in more detail. As used herein, the term "spectral characteristic" refers to a distinct property of the spectral filter which influences the ability of the spectral filter to select or eliminate at least one wavelength of light. As used herein, the term "polarization characteristic" refers to a distinct property of the polarization filter which influences the ability of the polarization filter to alter a polarization of the light.

In a further exemplary embodiment, at least one result of the vision testing procedure may be determined from the at least one assistive device used in the last test cycle, particularly determined from the at least one degree of the at least one assistive device of influencing the ability of the person to solve the at least one task used in the last test cycle.

As used herein, the term "last test cycle" refers to the latest test cycle being performed before the vision testing procedure is being stopped or terminated. Thereby, the at least one refractive value of the assistive device may be the result. In a further exemplary embodiment, the at least one result may be at least one refractive value of an optical lens, particularly configured for compensating the at least one refractive error of the at least one eye of the person. The term "optical lens" refers to a visual aid which is used for determining and/or correcting a defective vision of a person wearing the optical lens.

In a further exemplary embodiment, the optical lens may be selected from at least one of:

a spectacle lens;

a contact lens; or an intraocular lens.

Based on the "Standard," 3.5.2, the term "spectacle lens" refers to an optical lens which is used for determining and/or correcting a defective vision of a wearer of the optical lens, wherein the optical lens is carried in front of the eye of the person, thereby avoiding a direct contact with the eye of a wearer. As generally used, the term "contact lens" refers to a lens placed directly on the surface of the eye of the wearer to correct visual defects. As further generally used, the term "intraocular lens" refers to an artificial lens implanted in the eye of a wearer for correcting the defective vision.

In a further exemplary embodiment, the at least one action may be selected from at least one of:

giving a feedback to the person whether the at least one provided response was the expected response, particularly before presenting the at least one task in the at least one subsequent test cycle;

querying an indication on an estimate of the at least one certainty from the person, particularly before presenting the at least one task in the at least one subsequent test cycle;

changing the time-to-answer in the at least one subsequent test cycle;

maintaining the at least one presented task and presenting it again in the at least one subsequent test cycle;

changing the at least one presented task and presenting at least one further task in the subsequent test cycle which differs from the at least one presented task;

maintaining the used assistive device and using it again in the at least one subsequent test cycle;

changing the used assistive device and using at least one further assistive device in the subsequent test cycle which differs from the used assistive device;

changing at least one parameter of a symbol presented on the presentation device; particularly wherein the at least one parameter of the symbol is selected from at least one of:

a size, an orientation, a color, or a polarization of the symbol; and displaying a further symbol considering the changed parameter in at least one subsequent test cycle;

querying an indication on a change of a distance between the eye of the person and the displaying device from the person, particularly before presenting the at least one task in the at least one subsequent test cycle; or querying an indication on a change of an orientation between the eye of the person and the displaying device and or symbol from the person, particularly before presenting the at least one task in the at least one subsequent test cycle.

As used herein, the term "giving a feedback" refers to giving an indication to the person about the performance of the person within the vision testing procedure, particularly an indication about the response provided, particularly in the particular measurement cycle, being the expected response or not being the respected response. As used herein, the term "maintaining" a specific at least one action performed in the particular test cycle refers to repeating the specific at least one action in the subsequent test cycle. As used herein, the term "changing" a specific at least one action refers to adapting in the subsequent test cycle the at least one action performed in the particular test cycle, particularly be considering the at least one confidence value. As used herein, the term "symbol" refers to a structure that is used to test a visual parameter of the person. As used herein, the term "parameter of a symbol" refers to a value influences the appearance of the symbol, particularly when the parameter of the symbol changes then the appearance of the symbol also changes. As generally used, the term "polarization" refers to a property of transverse waves, particularly light waves, that specifies a geometrical orientation of at least one oscillation.

In a further exemplary embodiment, the at least one further task may have a different difficulty, particularly an increasing or a decreasing difficulty, specifically compared to the at least one presented task. As used herein, the term "different difficulty" may be related to a change of the presented symbol and/or at least one parameter of the presented symbol, particularly presented in the at least one particular test cycle. In a further exemplary embodiment, a difference of the difficulty between the at least one further task and the at least one presented task may correlate with the at least one determined confidence value. In particular, when the person is confident on giving the expected response, the change in in the difficulty between the at least one further task and the at least one presented task may be larger and/or smaller compared to a situation in which the person is unsure on giving the expected response.

In a further exemplary embodiment, the at least one further assistive device may have a different degree of influencing the ability of the person to solve the at least one task, specifically compared to the at least one used assistive device. The "used assistive device" may be the assistive device used in the particular test cycle. In a further exemplary embodiment, a difference of the degree between the at least one used assistive device and the at least one further assistive device may correlate with the at least one determined confidence value. In particular, when the person is unsure on giving the expected response, the change in the degree between the at least one used assistive device and the at least one further assistive device may be larger and/or smaller compared to a situation in which the person is confident on giving the expected response. In a further exemplary embodiment, the degree of the at least one further assistive device of influencing the ability of the person to solve the at least one task may be selected to improve the ability of the person to solve the task. As used herein, the term "improve the ability of the person to solve the task" may refer to the fact that the difficulty of the at least one task is counteracted by the assistive device.

In a further exemplary embodiment, the presentation device may be selected from at least one of:
an eye chart;
an electronic device, particularly selected from at least one of:
a screen;
a monitor;
a mobile communication device, specifically a smartphone;
a personal computer; or
a smartwatch.

As generally used, the term "eye chart" refers to a chart used to measure at least one of: a visual acuity; a contrast; or a color vision parameter. As used herein, the term "electronic device" refers to an apparatus requiring electric power to function. As generally used, the term "screen" refers to an electronic visual display device designated for the presentation of at least one of an image, an item, text, or a video transmitted electronically. As generally used, the term "monitor" refers to an electrically controlled display for a visual displaying of information such as an image or an item. As generally used, the term "personal computer" refers to a multi-purpose computer whose size, capabilities, and price make it feasible for an individual use. Personal computers are configured for being operated directly by an end user, rather than by a computer expert or a technician. As generally used, the term "smart watch" refers to an electronic wristwatch that has computer functionalities and connectivity and may, additionally, comprise at least one sensor and/or at least one actuator, for example at least one vibration motor.

In a further exemplary embodiment, querying the person to provide the expected response may be performed by using a querying device, particularly selected from at least one of: a screen or a speaker. As generally used, the term "speaker" refers to a sound transducers for converting at least one input signal into at least one mechanical vibration, particularly wherein the at least one mechanical vibration is perceptible as sound. The querying device may be identical to the presenting device.

In a further exemplary embodiment, at least one task may be selected from at least one of:
providing an indication about a type of at least one symbol;
providing an indication about at least one parameter of the at least one symbol, wherein the at least one parameter is selected from
an orientation;
a color;
a contrast; or
a polarization;
providing an indication about a number of a first plurality of the at least one symbol being presented on the presentation device and having a common feature, particularly wherein a second plurality of the at least one symbol is additionally presented on the presentation device and is not having the common feature.

As used herein, the term "type of at least one symbol" refers to the nature of the symbol, particularly the symbol being at least one of: a letter, a number, a sign, or an arrow. As used herein, the term "common feature" refers to an aspect of an appearance of a plurality of symbols in which the plurality of symbols are the same. A common feature may be the result of a common parameter of the plurality of symbols having the same aspect of the appearance. As generally used, the term "contrast" refers to a distinguishing feature for the brightness gradient of an image or between two pixels.

In a further exemplary embodiment, the difficulty of the at least one task may correlate with at least one of:
a size of the at least one symbol;
a complexity of the at least one symbol;
the orientation of the symbol;
the color of the symbol;
the contrast of the symbol; or
the polarization of the symbol.

As used herein, the term "complexity" may refer to an amount of details of the symbol. In a further exemplary embodiment, the at least one symbol may have a type being selected from at least one of: a letter; a number; or an arrow.

In a further exemplary embodiment, the measurement data recorded during at least one test cycle may be used as further training data in the computer-implemented method for further training of the machine learning model for determining the confidence value according to any one of the preceding aspects or exemplary embodiments. As used herein, the term "measurement data" refers to data that is recorded from an observation of the person performing the vision testing procedure, particularly by using an already trained machine learning model. As used herein, the term "further training" refers to an additional training being performed on the machine learning model that is already trained for determining the confidence level.

In a further exemplary embodiment, the measurement data may comprise at least one of the first information about at least one behavior of a person;

the second information about at least one known confidence value:

the third information about at least one known correctness value;

the fourth information about at least one known action; or the fifth information about the response as provided by the person.

In a further exemplary embodiment, the at least one further training data may comprise measurement data of at least 2; 3; 4; 5; 7; 10; 15; 20; 25; 50; 75; 100; 125; 150; 200; 500; 1000; 2000; 5000; 10000; 20000; 50000 test cycles.

In a further exemplary embodiment, the measurement data may be transmitted from a vision test apparatus to a training apparatus, particularly by using connecting interfaces, particularly wherein at least a portion of the measurement data may be recorded by the vision test apparatus, wherein the training apparatus may be performing the at least one further training. As used herein, the term "vision test apparatus" refers to a device used for performing the vision testing procedure, particularly comprising a processing device for running the machine learning model. As used herein, the term "training apparatus" refers to a device used for training of the machine learning model, particularly comprising a processing device for running the machine learning model. The training apparatus may be the vision test apparatus. As generally used, the term "connecting interface" or any grammatical variation thereof refers to an interface configured for transmitting data from a first apparatus to a second apparatus and/or receiving data with a second apparatus transmitted from a first apparatus. A typical connecting interface may be a network controller.

In a further exemplary embodiment, the updated machine learning model may be transmitted from the training apparatus to the vision test apparatus, particularly by using connecting interfaces, wherein the vision test apparatus may be performing further test cycles by using the updated trained machine learning model.

In a further exemplary embodiment, the data comprising the first information may be selected from at least one of:

audio data recorded by using the audio recording device;

visual data recorded by using the visual recording device;

tactile data recorded by using the tactile recording device; or distance data recorded by using the distance recording device.

In a further exemplary embodiment, the tactile recording device may be a touch screen. As generally used, the term "touch screen" refers to a combined input and output device that can be controlled by touching.

In a further exemplary embodiment, the visual data may be selected from at least one of:

an image; or a video;

particularly recorded during the time interval, more particularly recorded at a particular time interval at which the person is providing the response. As used herein, the term "image" refers to a single picture, particularly a picture of the person. As used herein, the term "video" refers to a plurality of images showing a scene.

In a further exemplary embodiment, the audio data may be processed before it is input into the machine learning model for determining an audio spectrogram of the audio data, particularly by using at least one of a Fourier transform method; or a wavelet transform method, particularly implemented by using a digital signal processor.

As generally used, the term "spectrogram" refers to a representation of the time course of a frequency spectrum of a signal by means of an image. As generally used, the term "digital signal processor" refers to an electronic component used for the processing of digital signals, particularly audio and/or video signals. As generally used, the term "Fourier transform method" refers to a process allowing for the analysis of complex waveforms in terms of their sinusoidal components. As generally used, the term "wavelet transform method" refers to a mathematical technique for decomposing a signal into multiple lower resolution levels by controlling the scaling and shifting factors of a single wavelet function.

In a further exemplary embodiment, the machine learning model may comprise a first input layer for the audio data into which the audio data, particularly the audio spectrogram, is input. As generally used, the term "input layer" refers to a layer into which the data to be processed by the neural network comprising the input layer is input.

In a further exemplary embodiment, the visual data may be processed before it is input into the machine learning model to extract a portion of the visual data comprising information about the face of the person, particularly by using at least one of selecting a specific subset of frames, particularly wherein the frames are selected that are recorded during the person is providing the response, more particularly wherein further frames are selected which are recorded within a predetermined time interval comprising the person providing the response;

a face landmark detection;

a face classification; or a cropping of the face, particularly based on the face landmark detection, particularly implemented by using a digital signal processor. As used herein, the term "extracting," or any grammatical variation thereof, refers to a procedure of selecting and further processing the portion of the visual data comprising information about the face of the person. As generally used, the term "face landmark detection" refers to detecting key landmarks on the face and tracking them. As generally used, the term "cropping," particularly of images, refers to a common photo manipulation process, by removing unwanted regions.

In a further exemplary embodiment, the machine learning model may comprise a second input layer for the visual data into which the visual data, particularly the portion of the visual data comprising information about the face of the person, is input.

In a further exemplary embodiment, the first input layer may forward information through a fourth encoding neural network, particularly selected from at least one of:

a convolutional neural network;

a VGG16;

a VGG19;

an Xception;

an InceptionV3;

a ResNet50;

a ResNet101;

a MobileNet; or a MobileNetV2.

As generally used, the term "encoding neural network" refers to a network for reducing and, thereby, encoding at least one input to a simplified feature representation. As generally used, the term "convolutional neural network" refers to a class of artificial neural networks. A convolutional neural network includes at least one layer that performs at least one convolution. The at least one convolution may be performed by a hidden layer. Reference is further made to the url keras.io/api/applications/(last accessed May 9, 2024) at which the different types of neural networks are defined. It should be noted that further neural network types may be feasible. The neurol networks may be implemented in any programming language.

In a further exemplary embodiment, the fourth encoding neural network may forward information into a first latent layer. As generally used, the term "latent layer" refers "refers to the last layer of an encoding neural network, which generates at least one output that is subsequently fed into a dense fusion layer for combining a plurality of latent layers, an output layer, or a decoding network.

In a further exemplary embodiment, the second input layer may forward information through a fifth encoding neural network, particularly selected from at least one of:

a convolutional neural network;

a VGG16;

a VGG19;

an Xception;

an InceptionV3;

a ResNet50;

a ResNet101;

a MobileNet; or a MobileNetV2.

In a further exemplary embodiment, the fifth encoding neural network may forward information into a second latent layer. In a further exemplary embodiment, at least one of:

the first latent layer; or the second latent layer, may forward information into a fusion layer. As used herein, the term "fusion layer" refers to a layer that merges the output of the first latent layer and/or second latent layer by generating a common output.

In a further exemplary embodiment, at least one of:

the fusion layer;

the first latent layer; or the second latent layer, may forward information through a first neural network having a first output layer, wherein the first output layer provides the at least one confidence value.

In a further exemplary embodiment, the first neural network may be selected from at least one of:

at least one layer dense network having at least two class softmax output heads; or at least one layer dense network having at least two linear output heads.

As generally used, the term "layer dense network" refers to a neural network having at least one dense layer. This dense layer may change, particularly decrease and/or increase, the dimension of the input layer of the neural network. As generally used, the term "softmax output head" refers to an output layer comprised by a neural network comprising at least two output nodes that provide a probability distribution over at least two classes. The two class softmax output head may be comprised by an output layer of the respective neural network. As generally used, the term "linear output head" refers to an output layer comprised by a neural network comprising at least one output node that provides a linear distribution, particularly continuous values. The two linear output heads may be comprised by an output layer of the respective neural network.

In a further exemplary embodiment, at least one of:

the fusion layer;

the first latent layer; or the second latent layer, may forward information through a second neural network having a second output layer, wherein the second output layer provides the at least one correctness value.

In a further exemplary embodiment, the second neural network may be selected from at least one of:

at least one layer dense network having at least two class softmax output heads; or at least one layer dense network having at least one linear output heads.

In a further exemplary embodiment, at least one of:

the first output layer; or the second output layer may forward information through a third neural network having a third output layer, wherein the third output layer provides the at least one action.

In a further exemplary embodiment, the third neural network may be selected from at least one of:

at least one layer dense network having at least two class softmax output heads.

In a further aspect, the present disclosure relates to a computer program comprising instructions which, when the program is executed by a computer, cause the computer to carry out the method according to any one of the preceding aspects or exemplary embodiments.

As generally used, the term "computer program" refers to at least one executable instruction for at least one programmable apparatus, specifically a computer, typically a sequence of executable instructions, for processing and/or solving of at least one function and/or at least one task and/or at least one problem by using at least one programmable apparatus, specifically a computer, typically for performing some or all steps of any one of the methods according to any aspect or exemplary embodiment as described within the present disclosure. Typically, instructions are combined to a computer program code and/or provided in a programming language. A computer program is typically processed by using a processing device comprised by the at least one computer. For this purpose, the computer program may be running on the computer. The computer program code may be provided on a data storage medium or a separate device such as an optical storage medium, e.g., on a compact disc, directly on a computer or data processing device, or via a network, such as via an in-house network or via internet. For further details concerning the computer program, a reference may be made to the methods according to the present disclosure as disclosed elsewhere herein.

In a further aspect, the present disclosure relates to a trained machine learning model which has been trained according to any one of the preceding aspects or exemplary embodiments. As used herein, the term "trained machine learning" refers to a model of the machine learning model, specifically comprising at least one neural network, that is trained, particularly that comprises parameters that are adapted for determining a confidence value during at least one test cycle of a vision testing procedure. The parameters of the machine learning model, particularly of the respective neural network, may be adapted by analyzing training data or further training data.

In a further aspect, the present disclosure relates to a training apparatus for training of a machine learning model for determining a confidence value during at least one test cycle of a vision testing procedure, wherein the training apparatus is configured to carry out a computer-implemented method for training of a machine learning model for determining a confidence value during at least one test cycle of a vision testing procedure, wherein the confidence value is designated for determining at least one action in at least one subsequent test cycle of the vision testing procedure; comprising the following steps:

a) providing training data, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

second information about at least one known confidence value, wherein the confidence value is a measure of a confidence level of the person at providing the expected response;

b) determining at least one confidence value of the person by analyzing the first information using a machine learning model, and determining a deviation between the determined confidence value and the at least one known confidence value as provided by the second information;

c) adjusting the machine learning model for minimizing the deviation between the determined confidence value and the at least one known confidence value;

wherein the steps a) to c) are repeated until a determination criterion is met.

In a further exemplary embodiment, the training apparatus may be further configured for carrying out a computer-implemented method for training of a machine learning model for determining a confidence value during at least one test cycle of a vision testing procedure according to any one of any one of the preceding aspects or exemplary embodiments.

In a further aspect, the present disclosure relates to a vision test apparatus for determining at least one visual parameter of a person, wherein the vision test apparatus is configured to carry out a computer-implemented method for performing a vision testing procedure on the person, wherein the vision test apparatus is configured to carry out a computer-implemented method for performing a vision testing procedure on a person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding aspects or exemplary embodiments by analyzing the first information by using a processing device; and g) determining at least one action in at least one subsequent test cycle of the vision testing procedure based on the determined confidence value by using the processing device.

In a further exemplary embodiment, the apparatus may be further configured to carry out a computer-implemented method for performing a vision testing procedure on a person according to any one of the preceding aspects or exemplary embodiments.

In a further exemplary embodiment, wherein the apparatus may be selected from at least one of:

a mobile communication device, specifically a smartphone;

a tablet; or a laptop.

As generally used, the term "tablet" refers to a portable, flat touch-screen computer. As generally used, the term "laptop" refers to a special type of computer having a screen movably attached to a housing, wherein the screen may be folded onto the housing.

In a further exemplary embodiment, the presentation device may be selected from at least one of:

an eye chart;

an electronic device, particularly selected from at least one of:

a screen;

a monitor;

a mobile communication device, specifically a smartphone;

a personal computer; or a smartwatch.

In a further exemplary embodiment, the screen may be selected from at least one of:

a virtual reality headset;

an augmented reality system;

a desktop computer;

a television set;

smart glasses; or a mobile communication device, specifically a smartphone.

As generally used, the term "virtual reality headset" refers to a head-mounted device that provides virtual reality for the wearer. As generally used, the term "augmented reality system" refers to a hardware for an interactive experience between a real-world environment and computer-generated perceptual information. As generally used, the term "desktop computer" refers to a computer in a housing shape suitable for use as a workstation computer on desks. As generally used, the term "television set" refers to a device or system having a tuner, a display and at least one loudspeaker for a purpose of viewing and listening to television broadcasting through at least one of satellite or cable, wherein the television set may also be used as a monitor. As generally used, the term "smart glasses" refers to wearable spectacles having computer functionality and may have connectivity. They may add information perceptible for the at least one eye of the person.

In a further exemplary embodiment, the audio recording device may be a microphone.

In a further exemplary embodiment, the visual recording device may be selected from at least one of:

a camera, particularly at least one of a front camera and/or a back camera of a mobile communication device, specifically selected from at least one of:
a smartphone;
a tablet; or
a smart watch;
a photocamera;
an infrared sensitive camera;
a webcam;
eye tracking glasses; or
a visually evoked potential device.

In a further exemplary embodiment, the tactile recording device may be a touch screen, particularly the at least one touch screen of the mobile communication device, specifically a smartphone. In a further exemplary embodiment, the apparatus comprises a querying device for querying the person to provide the expected response. In a further exemplary embodiment, the querying device may be selected from at least one of: a speaker; or a screen. In a further exemplary embodiment, the apparatus may comprise a data storage unit, particularly for storing at least one of:

the at least one confidence value;
the at least one correctness values;
the at least one action; or
the at least one presented task.

In a further aspect, the present disclosure relates to a method for producing a geometrical model of at least one spectacle lens for manufacturing of the at least one spectacle lens, wherein producing the geometrical model comprises producing a geometrical model of at least one spectacle lens for at least one eye of a person by using data related to at least one refractive value; and determining the data related to the at least one refractive value by carrying out a computer-implemented method for performing a vision testing procedure on a person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising
first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding aspects or exemplary embodiments by using a processing device; and g) determining at least one action in at least one subsequent test cycle of the vision testing procedure based on the determined confidence value by using the processing device.

As generally used, the term "producing" or any grammatical variation thereof refers to designing a geometrical model of at least one optical lens for at least one eye of a person. As used herein, the term "geometrical model of the spectacle lens" refers to a set of geometrical data of the at least one spectacle lens, particularly comprising exclusively geometrical data of the at least one spectacle lens. The geometrical data may be at least one radius of at least one curvature of the at least one spectacle lens to be manufactured. As generally used, the term "spectacle lens" refers to an optical lens, which is used for determining and/or correcting a defective vision of a wearer of the optical lens, wherein the optical lens is carried in front of the eye of the user, thereby avoiding a direct contact with the eye of a user, based on the Standard, 3.5.2.

In a further exemplary embodiment, the at least one spectacle is manufactured by processing at least one lens blank and considering the geometrical model of the at least one spectacle lens. In the process of manufacturing the at least one spectacle lens, a hard copy of the at least one spectacle lens is, eventually, made available to the person.

In a further exemplary embodiment, the data related to at least one refractive value may be determined by carrying out a computer-implemented method for performing a vision testing procedure on a person according to any one of the preceding aspects or exemplary embodiments.

Various exemplary embodiments may be conceived for implementing the methods according to the present disclosure. According to a first exemplary embodiment, all method steps may be performed by using a single processing device, such as a computer, especially a virtual reality headset, an augmented reality system, a desktop computer, a television set, smart glasses or a mobile communication device, specifically a smartphone. In this exemplary embodiment, the single processing device may be configured to exclusively perform at least one computer program, in particular at least one line of computer program code configured to execute at least one algorithm, as used in at least one of the methods according to the present disclosure. Herein, the computer program as executed on the single processing device may comprise all instructions causing the computer to carry out at least one of the methods according to the present disclosure. Alternatively or in addition, at least one method step may be performed by using at least one remote processing device, especially selected from at least one of a server or a cloud computer, which is not located at the site of the user when executing the at least one method step. In this further exemplary embodiment, the computer program may comprise at least one remote portion to be executed by the at least one remote processing device to carry out the at least one method step. Further, the computer program may comprise at least one interface configured to forward to and/or receive data from the at least one remote portion of the computer program.

With respect to the prior art, the present disclosure exhibits the following advantages.

The machine learning model is trained for determining the confidence value and/or correctness value, specifically for determining at least one action. Thereby, the behavior of the person is evaluated the person during a vision testing procedure, specifically a specific visual parameter of the at least one eye of the person. Thus, the respective measurement may be performed without guidance of a professional by the person alone. Alternatively, a professional may provide additional support.

As a result, the person on which the vision testing procedure is performed may trust more the results of the vision testing procedure, particularly as the vision testing procedure may feel more natural, especially owing to the dependency of the at least one action on the behavior of the person. Further, feedback may be provided to the person in a similar fashion as it is provided from a professional, particularly an optometrist, an ophthalmologist and/or or technician.

Due to the fact that the at least one action is based on the confidence value the vision testing procedure may be performed in less steps, thereby being performed faster, as the result may be approached faster.

As used herein, the terms "have," "comprise," or "include" or any arbitrary grammatical variation thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

As further used herein, the terms "typically," "more typically," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an exemplary embodiment" or similar expressions are intended to be optional features, without any restriction regarding alternative exemplary embodiments of the disclosure, without any restrictions regarding the scope of the disclosure and without any restriction regarding the possibility of combining the features introduced in this way with other features of the disclosure.

Clause 1: A computer-implemented method, particularly suitable, for training of a machine learning model for determining a confidence value during at least one test cycle of a vision testing procedure, wherein the confidence value is designated for determining at least one action in at least one subsequent test cycle of the vision testing procedure; comprising the following steps:

a) providing training data, comprising
first information about at least one behavior of a person during at least one test cycle of a vision testing procedure, wherein the at least one behavior of the person as provided by the first information is recorded from an observation of the person during a time interval after the person is queried to solve at least one task by providing an expected response;
second information about at least one known confidence value;

b) determining at least one confidence value of the person, wherein the confidence value is a measure of a confidence level of the person at providing the expected response, by analyzing the first information using a machine learning model, and determining a deviation between the determined confidence value and the at least one known confidence value as provided by the second information;

c) adjusting the machine learning model for minimizing the deviation between the determined confidence value and the at least one known confidence value;

wherein the steps a) to c) are repeated until a determination criterion is met.

Clause 2: The method according to any one of the preceding Clause, wherein the determination criterion is selected from:
the deviation being below a threshold;
a difference between the deviation determined in a training cycle and the deviation determined in a preceding training cycle being below a further threshold, wherein a training cycle comprises the steps a) to c);
a predetermined number of the training cycles is reached; or
an end of a predetermined training time interval is reached.

Clause 3: The method according to any one of the preceding Clauses, wherein an indication about the second information is obtained from at least one of:
a professional experienced in performing the vision testing procedure;
the person, particularly after being queried during the vision testing procedure to provide an indication about the confidence value;
monitoring at least one vital sign of the person, particularly wherein the at least one vital sign is selected from any one of a blood pressure or a heart-beat rate or a blink rate; or
a time value required for the person to provide the response, particularly the expected response.

Clause 4: The method according to any one of the preceding Clauses, wherein the professional is at least one of:
an optician;
an ophthalmologist;
a technician;
a psychologist; or
a nurse.

Clause 5: The method according to any one of the preceding Clauses, wherein the machine learning model is further trained for determining a correctness value, wherein the at least one correctness value is a measure of a probability that a response provided by the person is the expected response,
wherein the first information further comprises information about the response provided by the person, and
wherein the training data further comprises third information about at least one known correctness value;
wherein the at least one correctness value is determined by analyzing the first information using the machine learning model, wherein a first further deviation is determined between the determined correctness value and the known correctness value as provided by the third information, wherein the further training is repeated until a first further determination criterion is met.

Clause 6: The method according to any one of the preceding Clauses, wherein the first further determination criterion is selected from:
the first further deviation being below a further threshold;
a difference between the first further deviation determined in a training cycle and the first further deviation determined in a preceding training cycle being below a first further threshold, wherein a training cycle comprises the steps a) to c);
a predetermined first further number of the training cycles is reached; or
an end of a predetermined first further training time interval is reached.

Clause 7: The method according to any one of the preceding Clauses, wherein the machine learning model comprises a first neural network for determining the confidence value; and/or a second neural network for determining the correctness value, particularly wherein the first neural network differs from the second neural network.

Clause 8: The method according to any one of the preceding Clauses, wherein the machine learning model is further trained for determining at least one action in at least one subsequent test cycle of the vision testing procedure, wherein the training data further comprises fourth information about at least one known action, wherein the at least one action is determined by analyzing the determined at least one confidence value by using the machine learning model, wherein a further deviation is determined between the at least one determined action and the at least one known action provided by the fourth information, wherein the further training is repeated until a second further determination criterion is met.

Clause 9: The method according to any one of the preceding Clauses, wherein the second further determination criterion is selected from:

the second further deviation being below a further threshold;

a difference between the second further deviation determined in a training cycle and the second further deviation determined in a preceding training cycle being below a second further threshold, wherein a training cycle comprises the steps a) to c);

a predetermined second further number of the training cycles is reached; or an end of a predetermined second further training time interval is reached.

Clause 10: The method according to any one of the preceding Clauses, wherein the machine learning model further comprises a third neural network for determining the at least one action, particularly wherein the third neural network differs from the first neural network and from the second neural network.

Clause 11: The method according to any one of the preceding Clauses, wherein determining the at least one action comprises additionally analyzing the at least one correctness value.

Clause 12: The method according to any one of the preceding Clauses, wherein the fourth information about the at least one known action is determined in an assessment of the professional experienced in performing the vision testing procedure.

Clause 13: The method according to any one of the preceding Clauses, wherein the machine learning model is a machine learning model that is trained in a domain applicable to the vision testing procedure before it is trained for determining the at least one confidence value according to any one of the preceding Clauses.

Clause 14: The method according to any one of the preceding Clauses, wherein the domain applicable to the vision testing procedure is selected from at least one of:

voice classification or voice regression;

facial expression classification or facial expression regression; or body expression classification or body expression regression Clause 15: A computer-implemented method, particularly suitable, for performing a vision testing procedure on a person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding Exemplary embodiments by using a processing device; and g) determining at least one action in at least one subsequent test cycle of the vision testing procedure based on the determined confidence value.

Clause 16: The method according to any one of the preceding Clauses, wherein steps d) to f) are repeated in at least one subsequent test cycle using the at least one determined action.

Clause 17: The method according to any one of the preceding Clauses, wherein the confidence value is selected from at least one discrete scale, particularly wherein the confidence value is selected from at least two individual values; or at least one continuous scale, particularly wherein the continuous scale is ranging from the person being fully confident to the person being fully unsure.

Clause 18: The method according to the preceding Clause, wherein a first value of the confidence value represents the person being confident, and a second value of the confidence value represents the person being unsure about providing the expected response.

Clause 19: The method according to the preceding Clause, wherein the confidence value is selected from at least three individual values.

Clause 20: The method according to the preceding Clause, wherein a first value of the confidence value represents the person being confident, and a second value of the confidence value represents the person being neutral, and a third value of the confidence value represents the person being unsure about providing the expected response.

Clause 21: The method according to the preceding Clause, wherein the at least one known confidence value as provided by the second information has the same number of values as the determined confidence value; and wherein the individual values of the at least one known confidence value as provided by the second information represent the same piece of information about the confidence value as the values of the determined confidence value.

Clause 22: The method according to any one of the preceding Clauses, wherein the time interval starts at a first point of time when the person is queried to provide the expected response.

Clause 23: The method according to any one of the preceding Clauses, wherein the time interval ends at a second point of time after which the person has provided the response or at which a predetermined time-to-answer has expired.

Clause 24: The method according to any one of the preceding Clauses, wherein the at least one determined action is used in at least one consecutive test cycle.

Clause 25: The method according to any one of the preceding Clauses, wherein the at least one action is determined by at least one of the machine learning model trained by the method according to any one of the preceding Exemplary embodiments by using the processing device;

the professional performing the vision testing procedure; or a predetermined response-action scheme, particularly by using the processing device.

Clause 26: The method according to any one of the preceding Clauses, wherein the measurement data further comprises fifth information about the response as provided by the person.

Clause 27: The method according to the preceding Clause, wherein the fifth information is comprised by the first information.

Clause 28: The method according to any one of the preceding Clauses, wherein the at least one action is further based on at least one of:

the at least one correctness value; or a time value required for the person to provide the response, particularly the expected response;

the at least one presented task;

the progress of the visual testing procedure.

Clause 29: The method according to any one of the preceding Clauses, wherein at least one of the at least one confidence value;

the at least one correctness values;

the at least one action; or the at least one presented task is stored in a data storage unit.

Clause 30: The method according to any one of the preceding E Clauses, wherein the determining at least one action in at least one subsequent test cycle is further based on at least one of:

a predefined number of a plurality of confidence values;

a predefined number of a plurality of correctness values;

a predefined number of a plurality of actions; or a predefined number of a plurality of presented tasks particularly performed in at least 2, 5, 10, 20 or 30 different measurement.

Clause 31: The method according to any one of the preceding Clauses, wherein the least one correctness value is selected from at least two individual values.

Clause 32: The method according to any one of the preceding Clauses, wherein a first value represents the response as provided by the person is the expected response, a second value represents the response as provided by the person is not the expected response.

Clause 33: The method according to any one of the preceding Clauses, wherein the vision testing procedure is performed to determine at least one condition, particularly of at least one eye, of the person, particularly wherein the condition is an performance indicator of the vision of the person, particularly an impairment of the person.

Clause 34: The method according to any one of the preceding Clauses, wherein the at least one condition of the at least one eye of the person is at least one visual parameter of the at least one eye of the person.

Clause 35: The method according to any one of the preceding Clauses, wherein the at least one visual parameter is selected from at least one of a refractive error or a visual performance of the at least one eye of the person.

Clause 36: The method according to any one of the preceding Clauses, wherein the refractive error of the at least one eye of the person is at least one of a value related to:

a spherical power;

a cylindrical power;

a cylinder axis; or an addition power.

Clause 37: The method according to the any one of the preceding Clauses, wherein the visual performance is selected from at least one of a visual acuity, particularly selected from at least one of:

a near field visual acuity;

an intermediate visual acuity; or a far field visual acuity;

a contrast sensitivity; or a color vision; or a visual field.

Clause 38: The method according to the any one of the preceding Clauses, wherein the at least one expected response is at least one of:

a verbal indication of a solution of the at least one task;

a non-verbal indication of a solution of the at least one task.

Clause 39: The method according to the any one of the preceding Clauses, wherein the first information comprises only information recorded in a time interval during which the at least one person is providing the response.

Clause 40: The method according to the any one of the preceding Clauses, wherein the first information is processed in a pre-processing routine to comprise only information about a predetermined body-part of the person, particularly selected from at least one of: the face of the person; or the upper body of the person.

Clause 41: The method according to the any one of the preceding Clauses, wherein the first information is processed in a pre-processing routine to comprise only information about the person showing a predetermined at least one behavior.

Clause 42: The method according to the any one of the preceding Clauses, wherein the first information about the at least one behavior of the person comprises information about at least one of:

at least one expression in a body of the person, particularly at least one expression in a face of the person;

at least one expression in the voice of the person;

a characteristic behavior of a head of the person, particularly causing a movement of the head towards or away from the presentation device;

a characteristic behavior of a movement of the at least one eye of the person;

a characteristic behavior of an eyelid of the at least one eye of the person;

a characteristic behavior of at least one arm of the person.

Clause 43: The method according to the any one of the preceding Clauses, wherein the at least one expression in the body of the person is selected from at least one of:

at least one expression in the face of the person; particularly an expression of the at least one eye of the person, particularly an eye squinting of the person;

a scratching of the head, particularly by using a hand of the person; or the head of the person moving closer to or away from the presentation device, particularly for thereby adjusting a distance between the at least one eye of the person and the presentation device.

Clause 44: The method according to the any one of the preceding Clauses, wherein the at least one expression in the voice is selected from at least one of:

a volume;

a time duration;

an irregular pause;

a modulation;

a frequency or pitch, particularly a mean frequency or pitch; or a modulation.

Clause 45: The method according to any one of the preceding Clauses, wherein at least one recording device is selected from at least one of:

an audio recording device;

a visual recording device;

a tactile recording device; or a distance recording device.

Clause 46: The method according to the any one of the preceding Clauses, wherein the at least one expression in the voice of the person is recorded by using the audio recording device, particularly a microphone.

Clause 47: The method according to the any one of the preceding Clauses, wherein the at least one expression in the body of the person is recorded by using the visual recording device, particularly selected from at least one of:

a camera, particularly at least one of a front camera and/or a back camera of a mobile communication device, specifically selected from at least one of:

a smartphone;

a tablet; or a smart watch;

a photo-camera;

an infrared-camera;

a webcam;

eye tracking glasses; or a visually evoked potential device.

Clause 48: The method according to the any one of the preceding Clauses, wherein solving the at least one task is performed by the person using at least one assistive device, particularly at least one assistive device having a degree of influencing the ability of the person to solve the at least one task.

Clause 49: The method according to the any one of the preceding Clauses, wherein the at least one assistive device is configured to counteract the impairment of the person preventing the person to solve the at least one task.

Clause 50: The method according to the any one of the preceding Clauses, wherein at least one assistive device is selected from at least one of:

a visual aid, particularly spectacles, used by the person; or a phoropter;

a spectral filter;

a polarization filter; or a liquid optical lens device;

Clause 51: The method according to the any one of the preceding Clauses, wherein the degree of the at least one assistive device of influencing the ability of the person to solve the at least one task is selected from:

at least one refractive value of the visual aid used by the person when solving the at least one task;

at least one refractive value of the phoropter or the liquid optical lens used by the person when solving the at least one task;

at least one spectral characteristic of a spectral filter used by the person when solving the at least one task; or at least one polarization characteristic of a polarization filter used by the person when solving the at least one task.

Clause 52: The method according to the any one of the preceding Clauses, wherein at least one result of the vision testing procedure is determined from the at least one assistive device used in the last test cycle; particularly determined from the at least one degree of the at least one assistive device of influencing the ability of the person to solve the at least one task used in the last test cycle.

Clause 53: The method according to the any one of the preceding Clauses, wherein the at least one result is at least one refractive value of an optical lens, particularly configured for compensating the at least one refractive error of the at least one eye of the person.

Clause 54: The method according to the any one of the preceding Clauses, wherein the optical lens is selected from at least one of:

a spectacle lens;

a contact lens; or an intraocular lens.

Clause 55: The method according to the any one of the preceding Clauses, wherein the at least one action is selected from at least one of:

giving a feedback to the person whether the at least one provided response was the expected response, particularly before presenting the at least one task in the at least one subsequent test cycle;

querying an indication on an estimate of the at least one certainty from the person, particularly before presenting the at least one task in the at least one subsequent test cycle;

changing the time-to-answer in the at least one subsequent test cycle;

maintaining the at least one presented task and presenting it again in the at least one subsequent test cycle;

changing the at least one presented task and presenting at least one further task in the subsequent test cycle which differs from the at least one presented task;

maintaining the used assistive device and using it again in the at least one subsequent test cycle;

changing the used assistive device and using at least one further assistive device in the subsequent test cycle which differs from the used assistive device;

changing at least one parameter of a symbol presented on the presentation device; particularly wherein the at least one parameter is selected from at least one of:

a size, an orientation, a color, or a polarization;

and displaying a further symbol considering the changed parameter in at least one subsequent test cycle;

querying an indication on a change of a distance between the eye of the person and the displaying device from the person, particularly before presenting the at least one task in the at least one subsequent test cycle; or querying an indication on a change of an orientation between the eye of the person and the displaying device and or symbol from the person, particularly before presenting the at least one task in the at least one subsequent test cycle.

Clause 56: The method according to the any one of the preceding Clauses, wherein the at least one further task has a different difficulty, particularly an increasing or a decreasing difficulty, compared to the at least one presented task.

Clause 57: The method according to the any one of the preceding Clauses, wherein a variation of the difficulty between the at least one further task and the at least one presented task correlates with the at least one determined confidence value.

Clause 58: The method according to the any one of the preceding Clauses, wherein the at least one further assistive device has a different degree of influencing the ability of the person to solve the at least one task compared to the at least one used assistive device.

Clause 59: The method according to the any one of the preceding Clauses, wherein a variation of the degree between the at least one used assistive device and the at least one further assistive device correlates with the at least one determined confidence value.

Clause 60: The method according to the any one of the preceding Clauses, wherein the degree of the at least one further assistive device of influencing the ability of the person to solve the at least one task is selected to improve the ability of the person to solve the task.

Clause 61: The method according to the any one of the preceding Clauses, wherein the presentation device is selected from at least one of:
 an eye chart;
 an electronic device, particularly selected from at least one of:
  a screen;
  a monitor;
  a mobile communication device, specifically a smartphone;
  a personal computer; or
  a smartwatch.

Clause 62: The method according to the any one of the preceding Clauses, wherein querying the person to provide the expected response is performed by using a querying device, wherein the querying device is particularly selected from at least one of: a screen; or a speaker.

Clause 63: The method according to the any one of the preceding Clauses, wherein at least one task is selected from at least one of:
 providing an indication about a type of at least one symbol;
 providing an indication about at least one parameter of the at least one symbol, wherein the at least one parameter is selected from
 an orientation;
 a color;
 a contrast; or
 a polarization; or
 providing an indication about a number of a first plurality of the at least one symbol being presented on the presentation device and having a common feature, particularly wherein a second plurality of the at least one symbol is additionally presented on the presentation device and is not having the common feature.

Clause 64: The method according to the any one of the preceding Clauses, wherein the difficulty of the at least one task correlates with at least one of:
 a size of the at least one symbol;
 a complexity of the at least one symbol;
 the orientation of the symbol;
 the color of the symbol; or
 the contrast of the symbol.

Clause 65: The method according to the any one of the preceding Clauses, wherein the at least one symbol has a type being selected from at least one of:
 a letter;
 a number;
 a sign; or
 an arrow.

Clause 66: The method according to any one of the preceding Clauses, wherein the measurement data recorded during at least one test cycle is used as further training data in the computer-implemented method for further training of the machine learning model for determining the confidence value according to any one of the preceding Clauses.

Clause 67: The method according to any one of the preceding Clauses, wherein the measurement data comprises at least one of
 the first information about at least one behavior of a person;
 the second information about at least one known confidence value:
 the third information about at least one known correctness value;
 the fourth information about at least one known action; or
 the fifth information about the response as provided by the person.

Clause 68: The method according to any one of the preceding Clauses, wherein the at least one further training data comprises measurement data of at least 2; 3; 4; 5; 7; 10; 15; 20; 25; 50; 75; 100; 125; 150; 200; 500; 1000; 2000; 5000; 10000; 20000; 50000 test cycles.

Clause 69: The method according to any one of the preceding Clauses, wherein the measurement data are transmitted from a vision test apparatus to a training apparatus, particularly by using connecting interfaces, wherein at least a portion of the measurement data is recorded by the vision test apparatus, wherein the training apparatus is performing the at least one further training.

Clause 70: The method according to any one of the preceding Clauses, wherein the updated machine learning model is transmitted from the training apparatus to the vision test apparatus, particularly by using connecting interfaces, wherein the vision test apparatus is performing further test cycles by using the updated trained machine learning model.

Clause 71: The method according to any one of the preceding Clauses, wherein the data comprising the first information is selected from at least one of:
 audio data recorded by using the audio recording device;
 visual data recorded by using the visual recording device;
 tactile data recorded by using the tactile recording device; or
 distance data recorded by using the distance recording device.

Clause 72: The method according to any one of the preceding Clauses, wherein the tactile recording device is a touch screen;

Clause 73: The method according to any one of the preceding Clauses, wherein the visual data is selected from at least one of:
 an image; or
 a video;
particularly recorded during the time interval, more particularly recorded at a particular time interval at which the person is providing the response.

Clause 74: The method according to any one of the preceding Clauses, wherein the audio data is processed before it is input into the machine learning model for determining an audio spectrogram of the audio data, particularly by using at least one of a Fourier transform method; or a wavelet transform method, particularly implemented by using a digital signal processor.

Clause 75: The method according to any one of the preceding Clauses, wherein the machine learning model comprises a first input layer for the audio data into which the audio data, particularly the audio spectrogram, is input.

Clause 76: The method according to any one of the preceding Clauses, wherein the visual data is processed before it is input into the machine learning model to extract a portion of the visual data comprising information about the face of the person, particularly by using at least one of selecting a specific subset of frames, particularly wherein the frames are selected that are recorded during the person is providing the response, more particularly wherein further frames are selected which are recorded within a predetermined time interval comprising the person providing the response;

a face landmark detection;

a face classification; or a cropping of the face, particularly based on the face landmark detection, particularly implemented by using a digital signal processor.

Clause 77: The method according to any one of the preceding Clauses, wherein the machine learning model comprises a second input layer for the visual data into which the visual data, particularly the portion of the visual data comprising information about the face of the person, is input.

Clause 78: The method according to any one of the preceding Clauses, wherein the first input layer forwards information through a fourth encoding neural network, particularly selected from at least one of:

a convolutional neural network;

a VGG16;

a VGG19;

an Xception;

an InceptionV3;

a ResNet50;

a ResNet101;

a MobileNet; or a MobileNetV2.

Clause 79: The method according to any one of the preceding Clauses, wherein the fourth encoding neural network forwards information into a first latent layer.

Clause 80: The method according to any one of the preceding Clauses, wherein the second input layer forwards information through a fifth encoding neural network, particularly selected from at least one of:

a convolutional neural network;

a VGG16;

a VGG19;

an Xception;

an InceptionV3;

a ResNet50;

a ResNet101;

a MobileNet; or a MobileNetV2.

Clause 81: The method according to any one of the preceding Clauses, wherein the fifth encoding neural network forwards information into a second latent layer.

Clause 82: The method according to any one of the preceding Clauses, wherein at least one of:

the first latent layer; or the second latent layer, forwards information into a fusion layer.

Clause 83: The method according to any one of the preceding Clauses, wherein at least one of:

the fusion layer;

the first latent layer; or the second latent layer, forwards information through a first neural network having a first output layer, wherein the first output layer provides the at least one confidence value.

Clause 84: The method according to any one of the preceding Clauses, wherein the first neural network is selected from at least one of:

at least one layer dense network having an at least two class softmax output head; or at least one layer dense network having a linear output head.

Clause 85: The method according to any one of the preceding Clauses, wherein at least one of:

the fusion layer;

the first latent layer; or the second latent layer, forwards information through a second neural network having a second output layer, wherein the second output layer provides the at least one correctness value.

Clause 86: The method according to any one of the preceding Clauses, wherein the second neural network is selected from at least one of:

at least one layer dense network having an at least two class softmax output head; or at least one layer dense network having a linear output head.

Clause 87: The method according to any one of the preceding Clauses, wherein at least one of:

the first output layer; or the second output layer forwards information through a third neural network having a third output layer, wherein the third output layer provides the at least one action.

Clause 88: The method according to any one of the preceding Clauses, wherein the third neural network is selected from at least one of:

at least one layer dense network having an at least two class softmax output head; or at least one layer dense network having a linear output head.

Clause 89: A computer program comprising instructions which, when the program is executed by a computer, cause the computer to carry out the method according to any one of the preceding Clauses.

Clause 90: A trained machine learning model being trained according to any one of the preceding method Exemplary embodiments.

Clause 91: A training apparatus for training of a machine learning model for determining a confidence value during at least one test cycle of a vision testing procedure, wherein the training apparatus is configured to carry out a computer-implemented method for training of a machine learning model for determining a confidence value during at least one test cycle of a vision testing procedure, wherein the confidence value is designated for determining at least one action in at least one subsequent test cycle of the vision testing procedure; comprising the following steps:

a) providing training data, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

second information about at least one known confidence value, wherein the confidence value is a measure of a confidence level of the person at providing the expected response;

b) determining at least one confidence value of the person by analyzing the first information using a machine learning model, and determining a deviation between the determined confidence value and the at least one known confidence value as provided by the second information;

c) adjusting the machine learning model for minimizing the deviation between the determined confidence value and the at least one known confidence value;

wherein the steps a) to c) are repeated until a determination criterion is met.

Clause 92: The training apparatus according to any one of the preceding claims, wherein the training apparatus is further configured for carrying out a computer-implemented method for training of a machine learning model for determining a confidence value during at least one test cycle of a vision testing procedure according to any one of any one of the preceding Clauses.

Clause 93: A vision test apparatus for determining at least one visual parameter of a person, wherein the vision test apparatus is configured to carry out a computer-implemented method for performing a vision testing procedure on the person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding Clauses by analyzing the first information by using a processing device; and g) determining at least one action in at least one subsequent test cycle of the vision testing procedure based on the determined confidence value by using the processing device.

Clause 94: The training apparatus or the vison test apparatus according to any one of the preceding claims, wherein the apparatus is further configured to carry out a computer-implemented method for performing a vision testing procedure on a person according to any one of the preceding Clauses.

Clause 95: The training apparatus or the vison test apparatus according to any one of the preceding apparatus Exemplary embodiments, wherein the apparatus is selected from at least one of:

a mobile communication device, specifically a smartphone;

a tablet; or a laptop.

Clause 96: The training apparatus or the vison test apparatus according to any one of the preceding apparatus Exemplary embodiments, wherein the presentation device is selected from at least one of:

an eye chart;

an electronic device, particularly selected from at least one of:

a screen;

a monitor;

a mobile communication device, specifically a smartphone;

a personal computer; or a smartwatch.

Clause 97: The training apparatus or the vison test apparatus according to any one of the preceding apparatus Exemplary embodiments, wherein the screen is selected from at least one of:

a virtual reality headset;

an augmented reality system;

a desktop computer;

a television set;

smart glasses; or a mobile communication device, specifically a smartphone.

Clause 98: The training apparatus or the vison test apparatus according to any one of the preceding apparatus Exemplary embodiments, wherein the audio recording device is a microphone.

Clause 99: The training apparatus or the vison test apparatus according to any one of the preceding apparatus Exemplary embodiments, wherein the visual recording device is selected from at least one of:

a camera, particularly at least one of a front camera and/or a back camera of a mobile communication device, specifically selected from at least one of:

a smartphone;

a tablet; or a smart watch;

a photocamera;

an infrared sensitive camera;

a webcam;

eye tracking glasses; or a visually evoked potential device.

Clause 100: The training apparatus or the vison test apparatus according to any one of the preceding apparatus Exemplary embodiments, wherein the tactile recording device is a touch screen, particularly the at least one touch screen of the mobile communication device, specifically a smartphone.

Clause 101: The training apparatus or the vison test apparatus according to any one of the preceding apparatus Exemplary embodiments, wherein the apparatus comprises a querying device for querying the person to provide the expected response.

Clause 102: The training apparatus or the vison test apparatus according to any one of the preceding apparatus Exemplary embodiments, wherein the querying device selected from at least one of: a speaker; or a screen.

Clause 103: The training apparatus or the vison test apparatus according to any one of the preceding apparatus Exemplary embodiments, wherein the apparatus comprises a data storage unit, particularly for storing at least one of:

the at least one confidence value;

the at least one correctness values; or the at least one action.

Clause 104: A method for producing a geometrical model of at least one spectacle lens for manufacturing of the at least one spectacle lens, wherein producing the geometrical model comprises produce a geometrical model of at least one spectacle lens for at least one eye of a person by using data related to at least one refractive value; and determining the data related to the at least one refractive value by carrying out a computer-implemented method for performing a vision testing procedure on a person, wherein the vision testing procedure comprises at least two subsequent test cycles, wherein a test cycle comprises at least the following steps:

d) presenting at least one task to a person querying the person to provide an expected response by using a presentation device;

e) recording measurement data by using at least one recording device, comprising first information about at least one behavior of a person during at least one test cycle of a vision testing procedure, wherein the at least one behavior of the person as provided by the first information is recorded from an observation of the person during a time interval after the person is queried to solve at least one task by providing an expected response;

f) determining a confidence value of the person by analyzing the first information using a machine learning model being trained by the method according to any one of the preceding Clauses by using a processing device; and g) determining at least one action in at least one subsequent test cycle of the vision testing procedure based on the determined confidence value by using the processing device.

Clause 105: The method for producing at least one spectacle lens according to any one of the preceding claims, the at least one spectacle lens is manufactured by processing at least one lens blank by considering the produced geometrical model of the at least one spectacle lens.

Clause 106: The method for producing at least one spectacle lens according to any one of the preceding claims, wherein the data related to at least one refractive value is determined by carrying out a computer-implemented method for performing a vision testing procedure on a person according to any one of the preceding Clauses.

BRIEF DESCRIPTION OF THE DRAWINGS

Further optional features and exemplary embodiments of the present disclosure are disclosed in more detail in the subsequent description of exemplary embodiments. Therein, the respective optional features may be implemented in an isolated fashion as well as in any arbitrary feasible combination, as the skilled person will realize. It is emphasized here that the scope of the disclosure is not restricted by the exemplary embodiments.

The disclosure will now be described with reference to the drawings wherein:

FIG. 4 illustrates a schematic view of a further exemplary computer-implemented method for training of the machine learning model;

FIG. 5 illustrates a schematic view of an exemplary vision test apparatus and an exemplary training apparatus; and FIG. 6 illustrates a schematic view of method for producing a geometrical model of a spectacle lens for manufacturing the spectacle lens.

DESCRIPTION OF EXEMPLARY EMBODIMENTS

Figure 1:
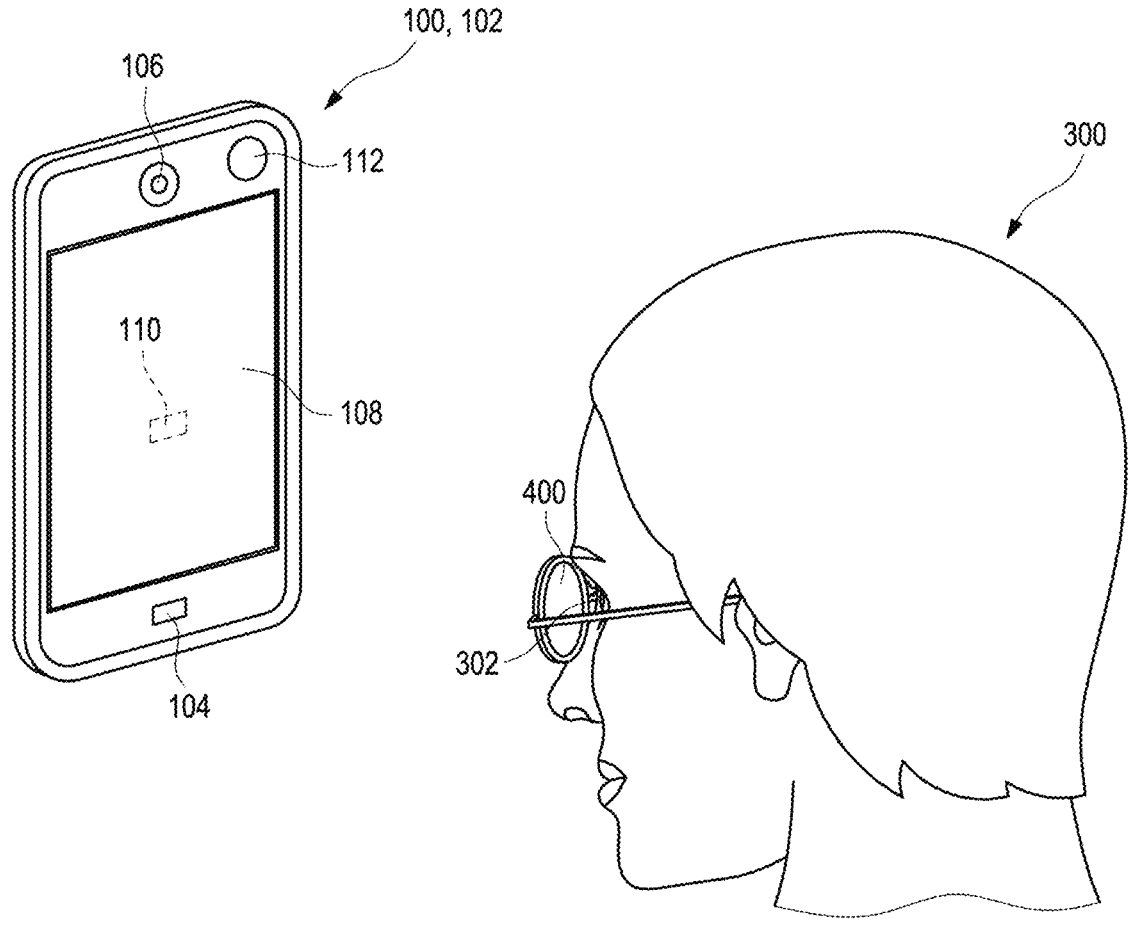
FIG. 1 illustrates an aerial view of an exemplary vision test apparatus for performing a vision testing procedure.

FIG. 1 illustrates an exemplary vision test apparatus 100 running a trained machine learning model 200, particularly processed by a processing device 110 of the vision test apparatus 100. The vision test apparatus 100 is configured for carrying out a computer-implemented method for performing a vision testing procedure 202 on the person 300. The vision testing procedure comprises at least two subsequent test cycles 204. The computer-implemented method 200 is described later in more detail.

The vision testing procedure may be performed to determine at least one condition, particularly of at least one eye 302, of the person 300, particularly wherein the condition is a performance indicator of the vision of the person, particularly an impairment of the person 300. The at least one condition of the at least one eye 302 of the person 300 may be the at least one visual parameter of the at least one eye 302 of the person 300.

The at least one visual parameter may be a refractive error or a visual performance of the at least one eye 302 of the person 300. The refractive error may be at least one a value related to a spherical power, a cylindrical power, a cylinder axis, and/or an addition power. The visual performance may be a visual acuity, particularly selected from at least one of a near field visual acuity, an intermediate visual acuity, or a far field visual acuity. The visual performance may, alternatively or in addition, be a contrast sensitivity, a color vision, and/or a visual field.

The vision test apparatus 100, as depicted in the exemplary embodiment of FIG. 1, is a mobile communication device, specifically a smartphone. Alternatively, the vision test apparatus 100 may be a tablet or a laptop. The person 300 is looking at the vision test apparatus 100 through an optional assistive device 400. The vision testing procedure may be performed without making use of the assistive device 400. The assistive device 400 as exemplarily depicted here is an optical lens, specifically a spectacle lens that is comprised by a spectacle frame.

During the vision testing procedure at least one task is presented to the person 300 on a presentation device 102. The presentation device 102 depicted in FIG. 1 is exemplarily an electronic device, specifically the mobile communication device, more specifically the smartphone. Alternatively, the presentation device 102 may be selected from an eye chart, or at least one further electronic device, specifically a screen, a monitor a personal computer and/or a smartwatch. The screen may be selected from a virtual reality headset, an augmented reality system, a desktop computer, a television set, smart glasses; or the mobile communication device, specifically the smartphone.

During the vision testing procedure the person 300 is queried to provide a response, specifically an expected response. Further, during the vision testing procedure the behavior of the person 300 is recorded and analyzed. Therefore, the apparatus 100 of the depicted exemplary embodiment comprises an audio recording device 104, particularly a microphone. As further depicted, the apparatus 100 comprises a visual recording device 106, particularly a front camera of the apparatus 100 being a smartphone, according to the exemplary embodiment. Alternatively, the visual recording device 106 may be a further and/or different camera, particularly a back camera of a further mobile communication device. Further alternatively, the visual recording device 106 may be a photocamera, an infrared sensitive camera, a webcam, eye tracking glasses and/or a visually evoked potential device. For receiving a response of the person 300 and/or recording an observation of the person 300, the apparatus 100 may further comprise a tactile recording device 108. As depicted, the tactile recording device 108 may be a touch screen, particularly of the exemplary mobile communication device. The vision test apparatus 100 may further comprise a distance recording device 112.

Figure 2:
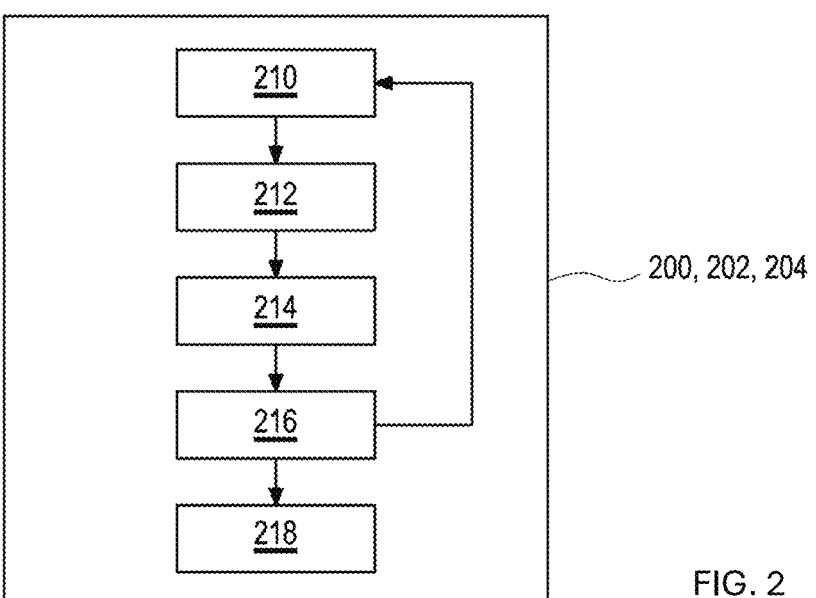
FIG. 2 illustrates a schematic view of an exemplary computer program running on the vision test apparatus comprising a computer-implemented method for performing the vision testing procedure.

The computer-implemented method, particularly suitable, for performing the vision testing procedure 202 on the person 300 is depicted in FIG. 2. The computer-implemented method is implemented as a computer program that is executed and/or running on the vision testing apparatus 100.

The vision testing procedure comprises at least two subsequent test cycles 204, wherein a test cycle 204 comprises at least the following steps:

d) presenting at least one task 210 to the person 300 querying the person 300 to provide an expected response by using a presentation device 102;

e) recording measurement data 212 by using at least one recording device, comprising first information about at least one behavior of the person 300 during at least one 204 of the vision testing procedure, wherein the at least one behavior of the person 300 as provided by the first information is recorded from an observation of the person 300 during a time interval after the person 300 is queried to solve at least one task by providing an expected response;

f) determining a confidence value 214 of the person 300 by analyzing the first information using a trained machine learning model 200; and g) determining at least one action 216 in at least one subsequent test cycle 204 of the vision testing procedure based on the determined confidence value.

The steps d) to g) may repeated in at least one subsequent test cycle 204 using the at least one determined action. The confidence value may be selected from at least one discrete scale, particularly wherein the confidence value is selected from at least two individual values, or at least one continuous scale, particularly wherein the continuous scale is ranging from the person 300 being fully confident to the person 300 being fully unsure. The at least one determined action may be used in at least one consecutive test cycle 204. The two individual values may be a first value of the confidence value representing the person 300 being confident, and/or a second value of the confidence value representing the person 300 being unsure about providing the expected response.

Alternatively, the confidence value may be selected from at least three individual values, wherein a first value of the confidence value represents the person 300 being confident, and/or wherein a second value of the confidence value represents the person 300 being neutral, and/or wherein a third value of the confidence value represents the person 300 being unsure about providing the expected response.

The at least one known confidence value as provided by the second information may have the same number of values as the determined confidence value; and/or the individual values of the at least one known confidence value as provided by the second information may represent the same piece of information about the confidence value as the values of the determined confidence value.

The time interval after the person 300 is queried to solve at least one task by providing an expected response may start at a first point of time when the person 300 is queried to provide the expected response. The time interval may end at a second point of time after which the person 300 has provided the response and/or at which a predetermined time-to-answer has expired.

The at least one action may be determined by the trained machine learning model 200, a professional performing the vision testing procedure and/or a predetermined response-action scheme. The professional may be an optician, an ophthalmologist, a technician, a psychologist and/or a nurse. The measurement data may further comprise fifth information about the response as provided by the person 300. The fifth information may be comprised by the first information. The at least one action may further be based on the at least one correctness value, or a time value required for the person 300 to provide the response, particularly the expected response, or the progress of the visual testing procedure, or the at least one presented task.

The at least one correctness value may be selected from at least two individual values, specifically from exactly two individual values. The individual values may be a first value that represents the response as provided by the person 300 is the expected response, and a second value that represents the response as provided by the person 300 is not the expected response. The at least one expected response may be a verbal indication of a solution of the at least one task, or a non-verbal indication of a solution of the at least one task.

The first information may comprise only information recorded in a time interval during which the at least one person 300 is providing the response. The first information may be processed in a pre-processing routine to comprise only information about a predetermined body-part of the person 300, particularly selected from at least one of: the face of the person 300; or the upper body of the person 300. The first information may be processed in a pre-processing routine to comprise only information about the person 300 showing a predetermined at least one behavior.

The first information about the at least one behavior of the person 300 may comprise information about at least one expression in a body of the person 300, particularly at least one expression in a face of the person 300. The first information about the at least one behavior of the person 300 may, additionally or alternatively, comprise information about at least one expression in the voice of the person 300 and/or a characteristic behavior of a head of the person 300, particularly causing a movement of the head towards or away from the presentation device 102. Additionally, or alternatively, the first information, may comprise information about a characteristic behavior of a movement of the at least one eye 302 of the person 300; a characteristic behavior of an eyelid of the at least one eye 302 of the person 300 and/or a characteristic behavior of at least one arm of the person 300.

The at least one expression in the body of the person 300 may be at least one expression in the face of the person 300, specifically an expression of the at least one eye 302 of the person 300, particularly an eye squinting of the person 300. The at least one expression in the body of the person may additionally or alternatively be a scratching of the head, particularly by using a hand of the person 300; or the head of the person 300 moving closer to or away from the presentation device 102, particularly for thereby adjusting a distance between the at least one eye 302 of the person 300 and the presentation device 102, specifically the presented and/or queried at least one task. The at least one expression in the voice may be a volume, a time duration, an irregular pause, a modulation, a frequency and/or pitch, particularly a mean frequency and/or pitch, and/or a modulation.

The at least one recording device may be an audio recording device 104, a visual recording device 106, a tactile recording device 108 and/or a distance recording device 112. The at least one expression in the voice of the person 300 may be recorded by using the audio recording device 104, particularly the microphone. The at least one expression in the body of the person 300 may be recorded by using the visual recording device 106.

Solving the at least one task may be performed by the person 300 using at least one assistive device 400, particularly at least one assistive device 400 having a degree of influencing the ability of the person 300 to solve the at least one task. The at least one assistive device 400 may be configured to counteract the impairment of the person 300 preventing the person 300 to solve the at least one task.

According to the exemplary embodiment depicted in FIG. 1, the at least one assistive device 400 is a visual aid used by the person 300, specifically an optical lens being a spectacle lens and being comprised by a spectacle. Alternatively, or in addition, the visual aid may be a phoropter, a spectral filter, a polarization filter and/or a liquid optical lens device. The optical lens may, alternatively, be a contact lens or an intraocular lens.

The degree of the at least one assistive device 400 of influencing the ability of the person 300 to solve the at least one task may be at least one refractive value of the visual aid 400 used by the person 300 when solving the at least one task, at least one refractive value of the phoropter or the liquid optical lens used by the person 300 when solving the at least one task, at least one spectral characteristic of a spectral filter used by the person 300 when solving the at least one task and/or at least one polarization characteristic of a polarization filter used by the person 300 when solving the at least one task.

At least one result of the vision testing procedure may be determined from the at least one assistive device 400 used in the last test cycle 204, particularly determined from the at least one degree of the at least one assistive device 400 of influencing the ability of the person 300 to solve the at least one task used in the last test cycle 204. The at least one result may be at least one refractive value of the optical lens, particularly configured for compensating the at least one refractive error of the at least one eye 302 of the person 300.

The at least one action may be giving a feedback to the person 300 whether the at least one provided response was the expected response, particularly before presenting at least one task in the at least one subsequent test cycle 204. Alternatively or in addition, the at least one action may be querying an indication on an estimate of the at least one certainty from the person 300, particularly before presenting the at least one task in the at least one subsequent test cycle 204, changing the time-to-answer in the at least one subsequent test cycle 204, maintaining the at least one presented task and presenting it again in the at least one subsequent test cycle 204, changing the at least one presented task and presenting at least one further task in the subsequent test cycle 204 that is different from the at least one presented task, maintaining the used assistive device 400 and using it again in the at least one subsequent test cycle 204 and/or changing the used assistive device 400 and using at least one further assistive device 400 in the subsequent test cycle 204 that is different from the used assistive device.

Alternatively, or in addition, the at least one action may be changing at least one parameter of a symbol presented on the presentation device 102 and displaying a further symbol considering the changed parameter in at least one subsequent test cycle 204. The changed parameter may be a size, an orientation, a color and/or a polarization. Alternatively, or in addition, the at least one action may be querying an indication on a change of a distance between the eye 302 of the person 300 and the displaying device from the person 300, particularly before presenting the at least one task in the at least one subsequent test cycle 204.

The at least one further task may have a different difficulty, particularly an increasing or a decreasing difficulty, compared to the at least one presented task. A variation of the difficulty between the at least one further task and the at least one presented task may correlate with the at least one determined confidence value. The at least one further assistive device 400 may have a different degree of influencing the ability of the person 300 to solve the at least one task compared to the at least one used assistive device 400. A variation of the degree between the at least one used assistive device 400 and the at least one further assistive device 400 may correlate with the at least one determined confidence value. The degree of the at least one further assistive device 400 of influencing the ability of the person 300 to solve the at least one task may be selected to improve the ability of the person 300 to solve the task.

The at least one task may be providing an indication about a type of the at least one symbol. Alternatively, or in addition, the at least one task may be providing an indication about at least one parameter of the at least one symbol, wherein the at least one parameter may be selected from an orientation, a color, a contrast, or a polarization. Alternatively, or in addition, the at least one task may be providing an indication about a number of a first plurality of the at least one symbol being presented on the presentation device 102 and having a common feature, particularly wherein a second plurality of the at least one symbol is additionally presented on the presentation device 102 and is not having the common feature.

The difficulty of the at least one task may correlate with a size of the at least one symbol, a complexity of the at least one symbol, the orientation of the symbol, the color of the symbol, and/or the contrast of the symbol. The at least one symbol may have a type that may be selected from a letter, a number, a sign, or an arrow.

The data comprising the first information may be audio data recorded by using the audio recording device 104, visual data recorded by using the visual recording device 106, tactile data recorded by using the tactile recording device 108 and/or distance data recorded by using the distance recording device 112. The visual data may be an image a video, particularly recorded during the time interval, more particularly recorded at a particular time interval at which the person 300 is providing the response.

Figure 3A:
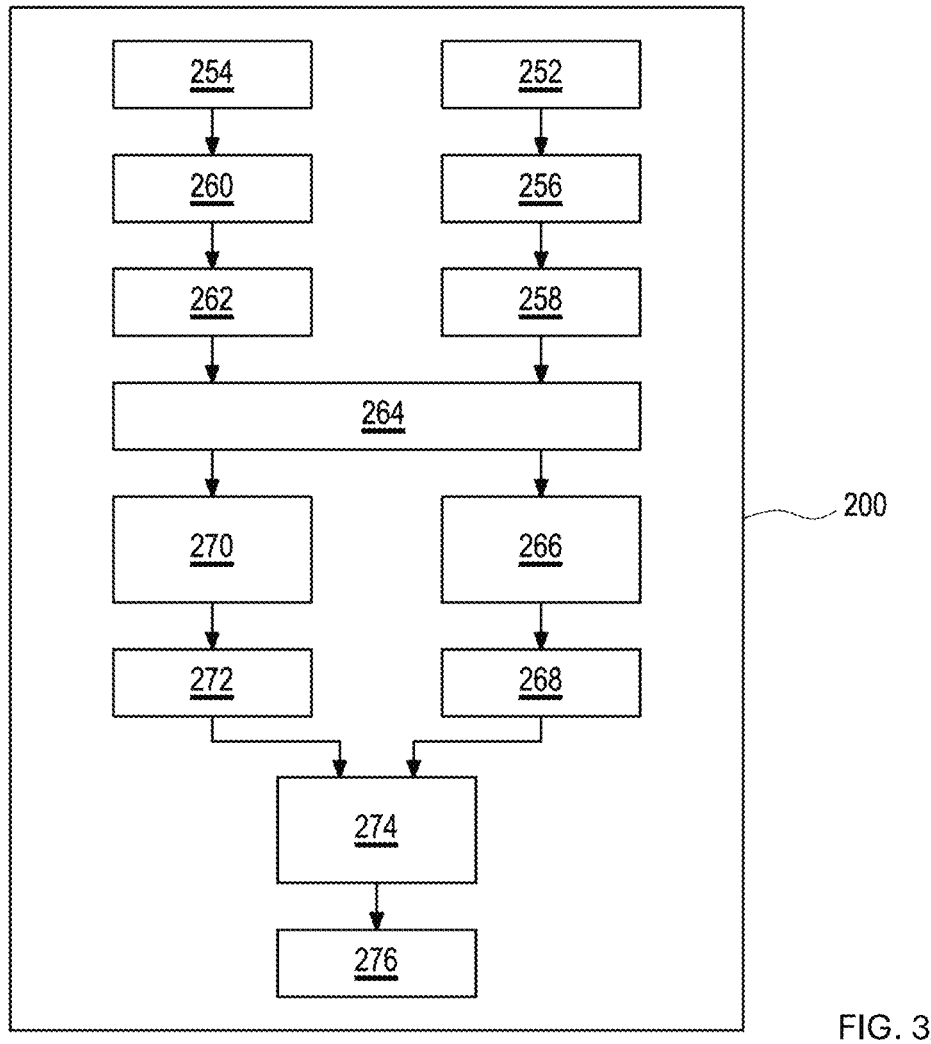
FIGS. 3A and 3B illustrate exemplary schematic views of machine learning models as comprised by the computer-implemented method.

As exemplarily being depicted in FIG. 3A, the computer-implemented method for performing the vision testing procedure 202 is implemented in a machine learning model 200 that comprises a first input layer 252 for the audio data into which the audio data, particularly an audio spectrogram, is input. The audio data may be processed before it is input into the machine learning model 200 for determining the audio spectrogram of the audio data, particularly by using a Fourier transform method; or a wavelet transform method, particularly implemented by using a digital signal processor.

The exemplary machine learning model 200 further comprises a second input layer 254 for the visual data into which the visual data, particularly the portion of the visual data comprising information about the face of the person 300, is input. The visual data may be processed before it is input into the machine learning model 200 to extract a portion of the visual data comprising information about the face of the person 300, particularly by selecting a specific subset of frames, particularly wherein the frames are selected that are recorded during the person is providing the response, more particularly wherein further frames are selected which are recorded within a predetermined time interval comprising the person providing the response, a face landmark detection; a face classification and/or a cropping of the face, particularly based on the face landmark detection. The extraction of the portion of the visual data may be implemented by using a digital signal processor. There may be further input layers for further input data.

The first input layer 252 forwards information through a fourth encoding neural network 256. The fourth encoding neural network 256 may be a convolutional neural network, a VGG16, a VGG19, an Xception, an InceptionV3, a ResNet50, a ResNet101, a MobileNet and/or a MobileNetV2. There may be further ways for implementing the fourth network 206. The fourth encoding neural network 256 forwards information into a first latent layer 258.

The second input layer 254 forwards information through a fifth encoding neural network 260. The fifth encoding neural network 260 may be may be a convolutional neural network, a VGG16, a VGG19, an Xception, an InceptionV3, a ResNet50, a ResNet101, a MobileNet and/or a Mobile-NetV2. The fifth encoding neural network 260 forwards information into a second latent layer 262.

The first latent layer 258 and the second latent layer 262 both forward information into a fusion layer 264. There may be further options in routing the information; particularly a further layer may forward information into the fusion layer 264.

The fusion layer 264 forwards information through a first neural network 266 having a first output layer 268, wherein the first output layer 268 provides the at least one confidence value. The information from the first latent layer 258 and/or the second latent layer 262 may alternatively be forwarded through and/or directly into the first neural network 266. Thereby, the fusion layer 264 may not be required. The first neural network 266 may be at least one layer dense network having at least two class softmax output heads or at least one layer dense network having at least two linear output heads.

The fusion layer 264 forwards information through a second neural network 270 having a second output layer 272, wherein the second output layer 272 provides the at least one correctness value. The second neural network 270 may not be required. The information from the first latent layer 258 and/or the second latent layer 262 may alternatively be forwarded through and/or directly into the second neural network 270. The second neural network 270 may be at least one layer dense network having at least two class softmax output heads or at least one layer dense network having at least two linear output heads.

The first output layer 268 and the second output layer 272 forwards information through a third neural network 274 having a third output layer 276, wherein the third output layer 276 provides the at least one action. The third neural network 274 may not be required. The third neural network 274 may be at least one layer dense network having at least two class softmax output head or at least one layer dense network having a linear output head.

Figure 3B:
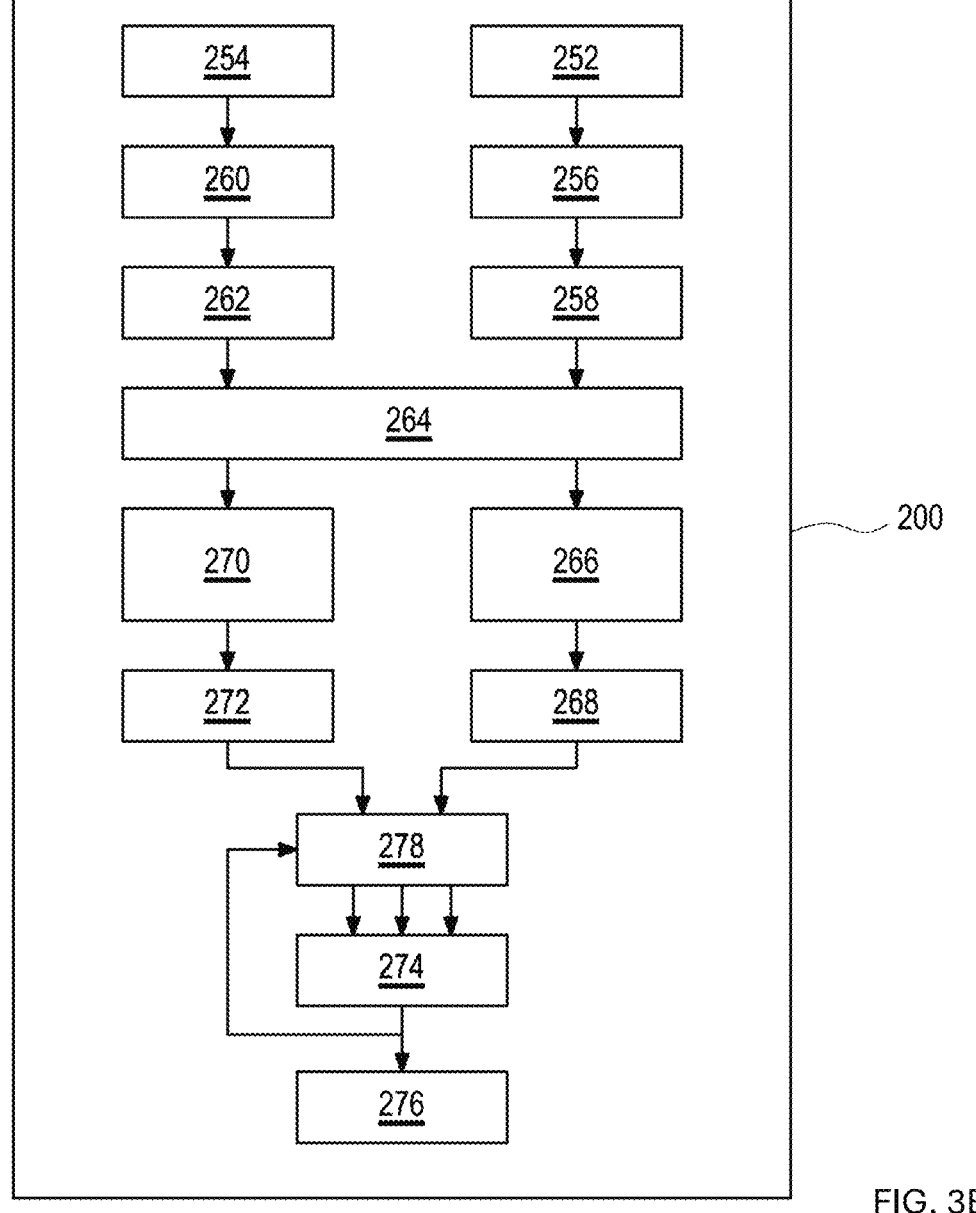

As exemplarily being depicted in FIG. 3B, the computer-implemented method for performing the vision testing procedure 202 is implemented in a further machine learning model 200. The further machine learning model 200 has the same components as the machine learning model 200 depicted in FIG. 3A, wherein reference to further details thereof can be made to the description of FIG. 3A above. In addition hereto, the further machine learning model 200 according to FIG. 3B further comprises a data storage unit 278 for storing at least one of: the at least one confidence value; the at least one correctness values; the at least one action; the at least one action particularly which may be determined in the current measurement cycle.

Therefore, the determining at least one action in at least one subsequent test cycle may then be based on taking into account at least one of:

a predefined number of a plurality of confidence values;
a predefined number of a plurality of correctness values;
a predefined number of a plurality of actions; or
a predefined number of a plurality of presented tasks, which may have particularly be performed in at least 2, 5, 10, 20, or 30 different measurements and may, typically, be input from the data storage unit 278 into the third neural network 274. In this manner, the progress of the visual testing procedure may also be recorded.

The discussed machine learning model 200 is a trained machine learning model 200. An exemplary computer-implemented method 500, particularly suitable, for training of the machine learning model 200 for determining a confidence value during at least one test cycle 204 of a vision testing procedure is depicted in FIG. 4. As depicted in FIG. 5, the training may be performed on a training apparatus 600 on which the exemplary computer-implemented method 500 for training of the machine learning model 200 is running and/or implemented. The training apparatus 600 may be the vision test apparatus 100. The confidence value is designated for determining at least one action in at least one subsequent test cycle 204 of the vision testing procedure; comprising the following steps:

a) providing training data 502, comprising
first information about at least one behavior of a person 300 during at least one test cycle 204 of a vision testing procedure, wherein the at least one behavior of the person 300 as provided by the first information is recorded from an observation of the person 300 during a time interval after the person 300 is queried to solve at least one task by providing an expected response;
second information about at least one known confidence value;
b) determining at least one confidence value 504 of the person 300, wherein the confidence value is a measure of a confidence level of the person 300 at providing the expected response, by analyzing the first information using a machine learning model 200, and determining a deviation 506 between the determined confidence value and the at least one known confidence value as provided by the second information;
c) adjusting 508 the machine learning model 200 for minimizing the deviation between the determined confidence value and the at least one known confidence value;

wherein the steps a) to c) are repeated until a determination criterion is met.

The determination criterion may be the deviation being below a threshold, a difference between the deviation determined in a training cycle and the deviation determined in a preceding training cycle being below a further threshold, wherein a training cycle comprises the steps a) to c). Alternatively or in addition, the determination criterion may be, a predetermined number of the training cycles being reached and/or an end of a predetermined training time interval is being reached.

An indication about the second information may be obtained from the professional experienced in performing the vision testing procedure and/or the person 300, particularly after being queried during the vision testing procedure to provide an indication about the confidence value. Alternatively or in addition, the indication about the second information may be obtained from monitoring at least one vital sign of the person 300, particularly wherein the at least one vital sign is selected from any one of a blood pressure, a heart-beat rate, or a blink rate. Alternatively or in addition, the indication about the second information may be obtained from a time value required for the person to provide the response, particularly the expected response.

The machine learning model 200 may further trained for determining a correctness value, wherein the at least one correctness value is a measure of a probability that a response provided by the person 300 is the expected response, wherein the first information further comprises information about the response provided by the person 300, and wherein the training data further comprises third information about at least one known correctness value;

wherein the at least one correctness value may be determined 510 by analyzing the first information using the machine learning model 200, wherein a first further deviation is determined 512 between the determined correctness value and the known correctness value as provided by the third information, wherein the machine learning model 200 is adjusted 514 for minimizing the first further deviation, wherein the further training is repeated until a first further determination criterion is met.

The first further determination criterion may be the first further deviation being below a further threshold and/or a difference between the first further deviation determined in a training cycle and the first further deviation determined in a preceding training cycle being below a first further threshold, wherein a training cycle comprises the steps a) to c). Alternatively or in addition, the first further determination criterion may be a predetermined first further number of the training cycles being reached and/or an end of a predetermined first further training time interval being reached.

The machine learning model 200 may, alternatively or in addition, further be trained for determining at least one action in at least one subsequent test cycle 204 of the vision testing procedure, wherein the training data further comprises fourth information about at least one known action, wherein the at least one action is determined 516 by analyzing the determined at least one confidence value by using the machine learning model 200, wherein a second further deviation is determined 518 between the at least one determined action and the at least one known action provided by the fourth information, wherein the machine learning model 200 is adjusted 520 for minimizing the second further deviation, wherein the further training is repeated until a second further determination criterion is met.

The second further determination criterion may be the second further deviation being below a further threshold and/or a difference between the second further deviation determined in a training cycle and the second further deviation determined in a preceding training cycle being below a second further threshold, wherein a training cycle comprises the steps a) to c). Alternatively or in addition, the second further determination criterion may be a predetermined second further number of the training cycles being reached and/or an end of a predetermined second further training time interval being reached.

Determining the at least one action may comprise additionally analyzing the at least one correctness value. The fourth information about the at least one known action may be determined in an assessment of the professional experienced in performing the vision testing procedure. The machine learning model 200 may be a machine learning model 200 that is trained in a domain applicable to the vision testing procedure before it is trained for determining the at least one confidence value. The domain applicable to the vision testing procedure may be selected from a voice classification or voice regression and/or a facial expression classification or facial expression regression and/or a body expression classification or body expression regression.

The measurement data recorded during at least one test cycle 204 is used as further training data in the computer-implemented method for further training of the machine learning model 200 for determining the confidence value. Thereby an updated machine learning model 200 may be provided The at least one further training data may comprise measurement data of at least 2; 3; 4; 5; 7; 10; 15; 20; 25; 50; 75; 100; 125; 150; 200; 500; 1000; 2000; 5000; 10000; 20000; or 50000 test cycles 204.

The measurement data may comprise the first information about at least one behavior of a person 300 and the second information about at least one known confidence value. The measurement data may additionally comprise the third information about at least one known correctness value and/or the fourth information about at least one known action and/or the fifth information about the response as provided by the person 300.

According to FIG. 5, the measurement data may be transmitted from a vision test apparatus 100 to a training apparatus 600, particularly by using connecting interfaces 120, 620, wherein at least a portion of the measurement data is recorded by the vision test apparatus 100, wherein the training apparatus 600 is performing the at least one further training. The updated machine learning model 200, particularly generated in the further training of the machine learning model 200, is transmitted from the training apparatus 600 to the vision test apparatus 100, particularly by using the connecting interfaces 120, 620, wherein the vision test apparatus 100 is performing further test cycles 204 by using the updated trained machine learning model.

As exemplarily depicted in FIG. 6, the disclosure also relates to a method for producing a geometrical model of at least one spectacle lens for manufacturing of the at least one spectacle lens 704, wherein producing the geometrical model comprises a step of producing a geometrical model of at least one spectacle lens 700 for at least one eye 302 of a person 300 by using data related to at least one refractive value; and determining the data related to the at least one refractive value by carrying out a computer-implemented method for performing a vision testing procedure on the person 300. The at least one spectacle lens may be manufactured in a step 702 of by processing at least one lens blank and considering the produced geometrical model of the at least one spectacle lens.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS 100 vision test apparatus
102 presentation device
104 audio recording device
106 visual recording device
108 tactile recording device
110 processing device
112 distance recording device
120 connecting interface
200 machine learning model
202 method for performing a vision testing procedure
204 test cycle
210 step d): presenting at least one task
212 step e): recording measurement data
214 step f): determining a confidence value
216 step g): determining at least one action
252 first input layer
254 second input layer
256 fourth encoding neural network
258 first latent layer
260 fifth encoding neural network
262 second latent layer
264 fusion layer
266 first neural network
268 first output layer
270 second neural network
272 second output layer
274 third neural network
276 third output layer
278 data storage unit
300 person
302 eye
400 assistive device
500 method for training of the machine learning model
502 step a): providing training data
504 part of step b): determining at least one confidence value
506 part of step b): determining a deviation
508 step c): adjusting the machine learning model
510 determine correctness value
512 determine first further deviation
514 adjust the machine learning model
516 determine at least one action
518 determine second further deviation
520 adjust the machine learning model
600 training apparatus
620 connecting interface
700 step of produce a geometrical model of at least one spectacle lens
702 step of manufacturing the at least one spectacle lens 704 method for producing a geometrical model of at least one spectacle lens for manufacturing of the at least one spectacle lens

The invention claimed is:

1. A computer-implemented method for training of a machine learning model for generating a trained machine learning model to determine a confidence value during a test cycle of a vision testing procedure, wherein the computer-implemented method is implemented as at least one computer program, wherein the confidence value is designated for determining an action in a subsequent test cycle of the vision testing procedure; the method comprising the following steps, which are performed by using the computer program:

a) providing training data including
　　first information about a behavior of a person during the test cycle of the vision testing procedure, wherein the behavior of the person as provided by the first information is recorded from an observation of the person during a time interval after the person is queried to solve a task by providing an expected response; and
　　second information about a known confidence value;

b) determining the confidence value of the person, wherein the confidence value is a measure of a confidence level of the person at providing the expected response, by analyzing the first information, using the machine learning model, and determining a deviation between the determined confidence value and the known confidence value as provided by the second information; and c) adjusting the machine learning model in order to minimize the deviation between the determined confidence value and the known confidence value by changing a parameter of the machine learning model, wherein the steps a) to c) are repeated until a determination criterion is met that, when met, leads to a termination of the training of the machine learning model, wherein the parameter of the machine learning model that resulted by determining a minimal deviation is used in the trained machine learning model, wherein the confidence value indicates how sure the person is in giving the expected response, wherein the vision testing procedure is performed for determining a condition of at least one eye of the person, wherein the condition is a performance indicator of the vision of the person, wherein the first information about the behavior of the person includes information about at least one of:
　　at least one expression in a body of the person; or
　　at least one expression in a voice of the person, wherein the confidence value is selected from:
　　at least one discrete scale; or
　　at least one continuous scale.

2. The method according to claim 1, wherein the machine learning model is further trained for generating the trained machine learning model to further determine a correctness value, wherein the correctness value is a measure of a probability that a response provided by the person is the expected response, wherein the first information further includes information about the response provided by the person, wherein the training data further includes third information about a known correctness value, wherein the correctness value is determined by analyzing the first information using the machine learning model, wherein a first further deviation is determined between the determined correctness value and the known correctness value as provided by the third information, wherein the parameters of the machine learning model are changed when at least a portion of the training data is analyzed by the machine learning model, wherein the further training is repeated until a first further determination criterion is met that, when met, leads to the termination of the further training of the machine learning model, and wherein the parameters of the machine learning model that resulted by determining a minimal first further deviation are used in the trained machine learning model.

3. The method according to claim 1, wherein the machine learning model is further trained for generating the trained machine learning model to further determine the action in the subsequent test cycle of the vision testing procedure, wherein the training data further comprises:

fourth information about a known action,
wherein the action is determined by analyzing the determined confidence value by using the machine learning model, wherein a second further deviation is determined between the determined action and the action provided by the fourth information, wherein the parameters of the machine learning model are changed when at least a portion of the training data is analyzed by the machine learning model, wherein the further training is repeated until a second further determination criterion is met that, when met, leads to the termination of the further training of the machine learning model, and wherein parameters of the machine learning model that resulted by determining a minimal second further deviation are used in the trained machine learning model.

4. The trained machine learning model, wherein the machine learning model has been trained by the computer-implemented method for training of the machine learning model according to claim 1.

5. The computer-implemented method for performing the vision testing procedure on the person, wherein the vision testing procedure includes at least two subsequent test cycles, wherein a subsequent test cycle comprises at least the following steps:

d) presenting the task to a person querying the person to provide an expected response by using a presentation device;
e) recording measurement data by using a recording device, including
the first information about the behavior of the person during the test cycle of the vision testing procedure, wherein the behavior of the person as provided by the first information is recorded from an observation of the person during the time interval after the person is queried to solve the task by providing the expected response;
f) determining the confidence value of the person by analyzing the first information using the machine learning model being trained by the method according to claim 1 by using the processing device; and
g) determining the action in the subsequent test cycle of the vision testing procedure by considering the determined confidence value.

6. The method according to claim 1, wherein the performance indicator of the vision of the person is an impairment of the person being expressed by a visual parameter of the at least one eye of the person, and wherein the visual parameter is selected from at least one of a refractive error or a visual performance of the at least one eye of the person.

7. The method according to claim 1, wherein solving the task is performed by the person using an assistive device, wherein the assistive device has a degree of influencing the ability of the person to solve the task, wherein the assistive device is configured to counteract an impairment of the person impeding the person to solve the task.

8. The method according to claim 1, wherein the determined action is selected from at least one of:

giving a feedback to the person whether the provided response was the expected response, optionally before presenting the task in the subsequent test cycle;
querying an indication on an estimate of at least one certainty from the person, optionally before presenting the at least one task in the at least one subsequent test cycle;
changing a time-to-answer in the at least one subsequent test cycle;
maintaining a presented task and presenting the presented task again in the subsequent test cycle;
changing the presented task and presenting a further task in the subsequent test cycle which differs from the presented task;
maintaining a used assistive device and using the used assistive device again in the subsequent test cycle;
changing the used assistive device and using a further assistive device in the subsequent test cycle which differs from the used assistive device;
changing a parameter of a symbol presented on a presentation device;
optionally wherein the parameter is selected from at least one of:
a size,
an orientation,
a color, or
a polarization
of the symbol; and displaying a further symbol considering the changed parameter in the subsequent test cycle; or
querying an indication on a change of a distance between at least one eye of the person and a displaying device from the person, optionally before presenting the task in the subsequent test cycle.

9. The method according to claim 8, wherein the further task has a different difficulty, optionally an increasing or a decreasing difficulty, compared to the presented task, wherein a variation of the difficulty between the further task and the presented task correlates with the determined confidence value.

10. The method according to claim 8, wherein the further assistive device has a different degree of influencing an ability of the person to solve the task compared to the used assistive device, and wherein a variation of a degree between the used assistive device and the further assistive device correlates with the determined confidence value.

11. The computer program having instructions which, when the program is executed by the computer, cause the computer to carry out the computer-implemented method according to claim 1 for performing a vision testing procedure on the person, wherein the vision testing procedure comprises the at least two subsequent test cycles, wherein the test cycle includes at least the following steps:

d) presenting the task to the person querying the person to provide the expected response by using the presentation device;
e) recording measurement data by using the recording device, including the first information about the behavior of the person during the test cycle of the vision testing procedure, wherein the behavior of the person as provided by the first information is recorded from the observation of the person during the time interval after the person is queried to solve the task by providing the expected response;

f) determining the confidence value of the person by analyzing the first information using the machine learning model being trained by the method by using the processing device; and g) determining the action in the subsequent test cycle of the vision testing procedure by considering the determined confidence value.

12. A vision test apparatus for determining the visual parameter of the person, wherein the vision test apparatus is configured to carry out the computer-implemented method for performing the vision testing procedure on the person, wherein the vision testing procedure includes the at least two subsequent test cycles, wherein the test cycle comprises at least the following steps:

d) presenting at least one task to the person querying the person to provide the expected response by using a presentation device;

e) recording measurement data by using at least one recording device, including the first information about the behavior of the person during the at least one test cycle of the vision testing procedure, wherein the behavior of the person as provided by the first information is recorded from the observation of the person during the time interval after the person is queried to solve the at least one task by providing the expected response;

f) determining the confidence value of the person by analyzing the first information using the machine learning model being trained by the method according to claim 1 by analyzing the first information by using a processing device; and g) determining at least one action in the at least one subsequent test cycle of the vision testing procedure by considering the determined confidence value by using the processing device.

13. A method for producing a geometrical model of at least one spectacle lens for manufacturing of the at least one spectacle lens, wherein producing the geometrical model comprises:

determining data related to at least one refractive value by carrying out the computer-implemented method for performing the vision testing procedure on the person by using the computer, wherein the vision testing procedure includes at least two subsequent test cycles, wherein the test cycle includes at least the following steps:

d) presenting at least one task to the person querying the person to provide an expected response by using a presentation device;

e) recording measurement data by using at least one recording device, including the first information about the behavior of the person during at least one test cycle of the vision testing procedure, wherein the behavior of the person as provided by the first information is recorded from an observation of the person during a time interval after the person is queried to solve at least one task by providing an expected response;

f) determining the confidence value of the person by analyzing the first information using the machine learning model being trained by the method according to claim 1 by using a processing device; and g) determining at least one action in at least one subsequent test cycle of the vision testing procedure based on the determined confidence value by using the processing device; and producing the geometrical model of the at least one spectacle lens for the at least one eye of the person by using the data related to the at least one refractive value by using the computer, a server or a cloud.

14. The method according to claim 1, wherein the confidence level selected from the at least one discrete scale is selected from at least two individual values.

15. The method according to claim 1, wherein the at least one continuous scale ranges from the person being fully confident to the person being fully unsure.

16. A computer program having instructions which, when the program is executed by a computer, cause the computer to carry out a computer-implemented method for training of a machine learning model for generating a trained machine learning model to determine a confidence value during a test cycle of a vision testing procedure, wherein the computer-implemented method is implemented as the computer program, wherein the confidence value is designated for determining an action in a subsequent test cycle of the vision testing procedure; comprising the following steps, which are performed by using the computer program:

a) providing training data, the training data including first information about a behavior of a person during the test cycle of the vision testing procedure, wherein the behavior of the person as provided by the first information is recorded from an observation of the person during a time interval after the person is queried to solve a task by providing an expected response; and second information about a known confidence value, wherein the known confidence value is a measure of a confidence level of the person at providing the expected response;

b) determining the confidence value of the person by analyzing the first information using the machine learning model, and determining a deviation between the determined confidence value and the known confidence value as provided by the second information; and c) adjusting the machine learning model in order to minimize a deviation between the determined confidence value and the known confidence value by changing a parameter of the machine learning model;

wherein the steps a) to c) are repeated until a determination criterion is met that, when met, leads to a termination of the training of the machine learning model, wherein the parameter of the machine learning model that resulted by determining a minimal deviation is used in the trained machine learning model, wherein the confidence value indicates how sure the person is in giving the expected response, wherein the vision testing procedure is performed for determining a condition of at least one eye of the person, wherein the condition is a performance indicator of the vision of the person, wherein the first information about the behavior of the person includes information about at least one of:

at least one expression in a body of the person; or at least one expression in a voice of the person, and wherein the confidence value is selected from:

at least one discrete scale; or at least one continuous scale.

17. A training apparatus for training of a machine learning model for determining a confidence value during a test cycle of a vision testing procedure, wherein the training apparatus is configured to carry out a computer-implemented method for training of the machine learning model for generating a trained machine learning model for determining the confidence value during the test cycle of the vision testing procedure, the computer-implemented method being implemented as at least one computer program, wherein the confidence value is designated for determining an action in a subsequent test cycle of the vision testing procedure; comprising the following steps, which are performed by using the computer program:

a) providing training data, including first information about a behavior of the person during the test cycle of the vision testing procedure, wherein the behavior of a person as provided by the first information is recorded from an observation of the person during a time interval after the person is queried to a task by providing an expected response; and second information about a known confidence value, wherein the confidence value is a measure of a confidence level of the person at providing the expected response;

b) determining the confidence value of the person by analyzing the first information using the machine learning model, and determining a deviation between the determined confidence value and the known confidence value as provided by the second information; and c) adjusting the machine learning model in order to minimize the deviation between the determined confidence value and the known confidence value by changing a parameter of the machine learning model, wherein the steps a) to c) are repeated until a determination criterion is met that, when met, leads to a termination of the training of the machine learning model, wherein the parameter of the machine learning model that resulted by determining the minimal deviation is used in the trained machine learning model, wherein the confidence value indicates how sure the person is in giving the expected response, and wherein the vision testing procedure is performed for determining a condition of at least one eye of the person, wherein the condition is a performance indicator of the vision of the person, and wherein the first information about the behavior of the person includes information about at least one of:

at least one expression in a body of the person; or at least one expression in a voice of the person, and wherein the confidence value is selected from:

at least one discrete scale; or at least one continuous scale.

18. A computer-implemented method for training of a machine learning model for generating a trained machine learning model to determine a confidence value during a test cycle of a vision testing procedure, wherein the computer-implemented method is implemented as at least one computer program, wherein the confidence value is designated for determining an action in a subsequent test cycle of the vision testing procedure; the method comprising the following steps, which are performed by using the computer program:

h) providing training data including first information about a behavior of a person during the test cycle of the vision testing procedure, wherein the behavior of the person as provided by the first information is recorded from an observation of the person during a time interval after the person is queried to solve a task by providing an expected response; and second information about a known confidence value;

i) determining the confidence value of the person, wherein the confidence value is a measure of a confidence level of the person at providing the expected response, by analyzing the first information, using the machine learning model, and determining a deviation between the determined confidence value and the known confidence value as provided by the second information; and j) adjusting the machine learning model in order to minimize the deviation between the determined confidence value and the known confidence value by changing a parameter of the machine learning model, wherein the steps h) to j) are repeated until a determination criterion is met that, when met, leads to a termination of the training of the machine learning model, wherein the parameter of the machine learning model that resulted by determining a minimal deviation is used in the trained machine learning model, and giving a feedback to the person whether the provided response was the expected response, optionally before presenting the task in the subsequent test cycle;

querying an indication on an estimate of at least one certainty from the person, optionally before presenting the at least one task in the at least one subsequent test cycle;

changing a time-to-answer in the at least one subsequent test cycle;

maintaining a presented task and presenting the presented task again in the subsequent test cycle;

changing the presented task and presenting a further task in the subsequent test cycle which differs from the presented task;

maintaining a used assistive device and using the used assistive device again in the subsequent test cycle;

changing the used assistive device and using a further assistive device in the subsequent test cycle which differs from the used assistive device;

changing a parameter of a symbol presented on a presentation device;

optionally wherein the parameter is selected from at least one of:

a size, an orientation, a color, or a polarization of the symbol; and displaying a further symbol considering the changed parameter in the subsequent test cycle; and querying an indication on a change of a distance between at least one eye of the person and a displaying device from the person, optionally before presenting the task in the subsequent test cycle.

* * * * *